United States Patent [19]
Aoki et al.

[11] Patent Number: 6,084,715
[45] Date of Patent: Jul. 4, 2000

[54] IMAGE-FORMING OPTICAL SYSTEM AND APPARATUS USING THE SAME

[75] Inventors: Norihiko Aoki, Iino-machi; Takayoshi Togino, Koganei; Akira Tamagawa, Hachioji, all of Japan

[73] Assignee: Olympus Optical Co., Ltd., Tokyo, Japan

[21] Appl. No.: 09/313,389

[22] Filed: May 18, 1999

[30] Foreign Application Priority Data

May 19, 1998 [JP] Japan .................................. 10-136844

[51] Int. Cl.[7] ............................ G02B 27/10; G02B 27/14
[52] U.S. Cl. .......................... 359/627; 359/630; 359/631
[58] Field of Search .................................... 359/629–638

[56] References Cited

U.S. PATENT DOCUMENTS 6,021,004  2/2000  Sekita ...................................... 359/676

FOREIGN PATENT DOCUMENTS 8-292368  11/1996  Japan .
8-292371  11/1996  Japan .

*Primary Examiner*—Georgia Epps
*Assistant Examiner*—Michael A Lucas
*Attorney, Agent, or Firm*—Pillsbury Madison & Sutro LLP

[57] ABSTRACT

A compact, thin and low-cost image-forming optical system having an optical low-pass filter, and an apparatus using the image-forming optical system. The image-forming optical system for forming an image of an object includes a stop (2), a first prism (10) placed closer to the object side than the stop (2), and a second prism (20) placed closer to the image side than the stop (2). The first prism (10) has object-side reflecting surfaces (12, 13) with an aspherical surface configuration that reflect a light beam in the prism and give a power to the light beam when reflecting it. The second prism (20) has image-side reflecting surfaces (22, 23) with an aspherical surface configuration that reflect a light beam in the prism and give a power to the light beam when reflecting it. A low-pass filter (4) for cutting off a high-frequency component is provided between the object-side reflecting surfaces (12, 13) and the image-side reflecting surfaces (22, 23).

20 Claims, 17 Drawing Sheets

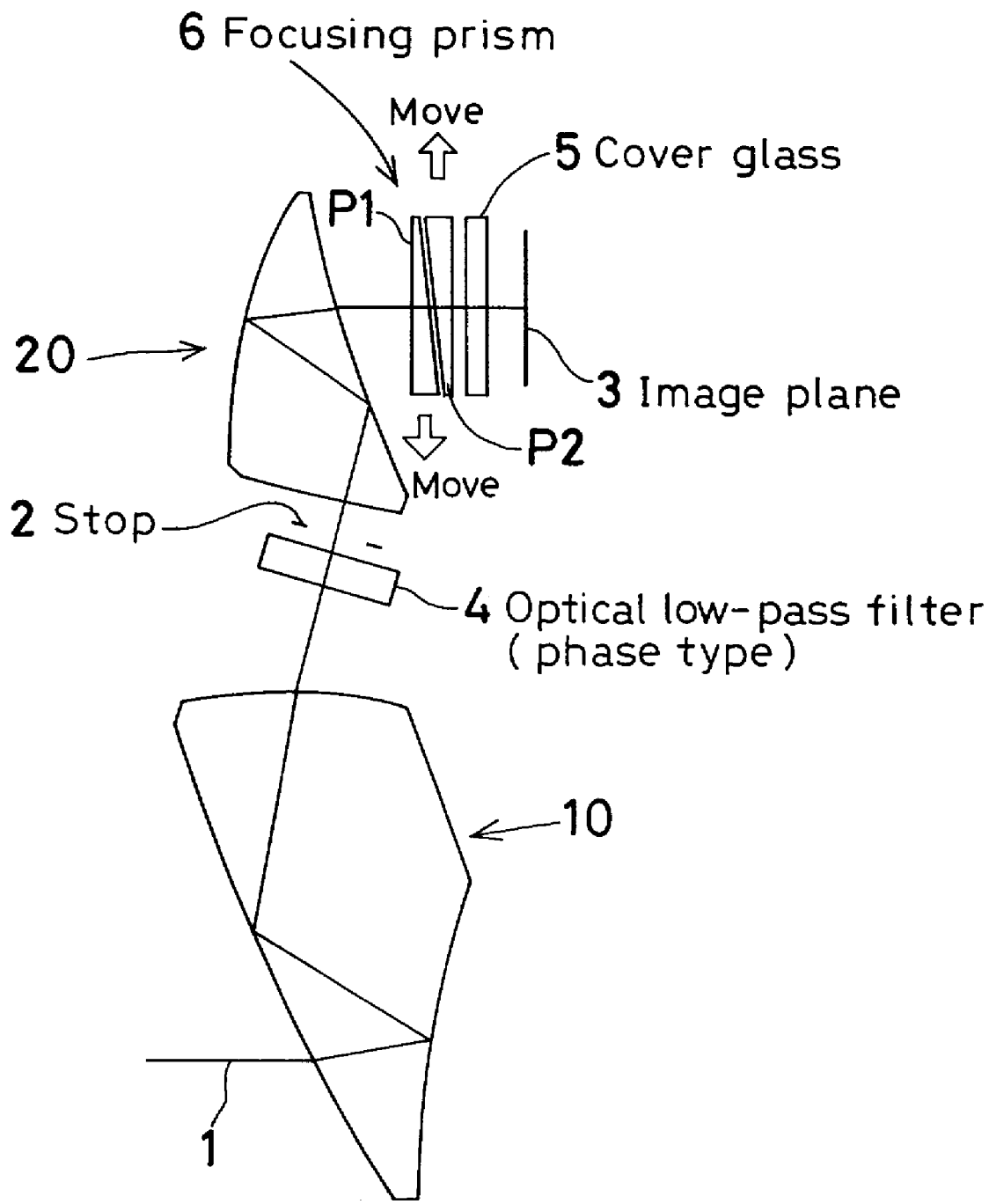

FIG. 6(a)
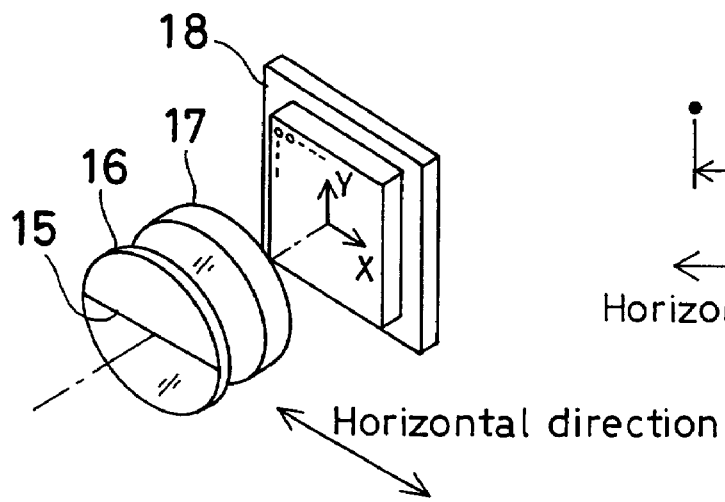
FIG. 6(b)
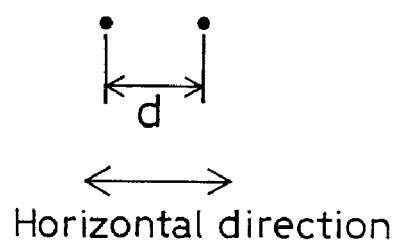
Horizontal direction
FIG. 7
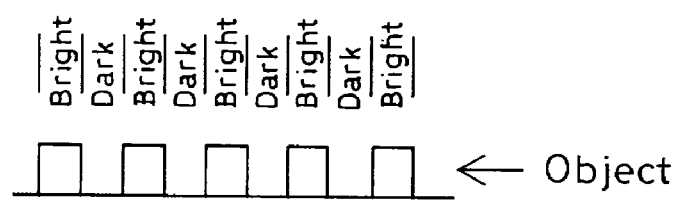
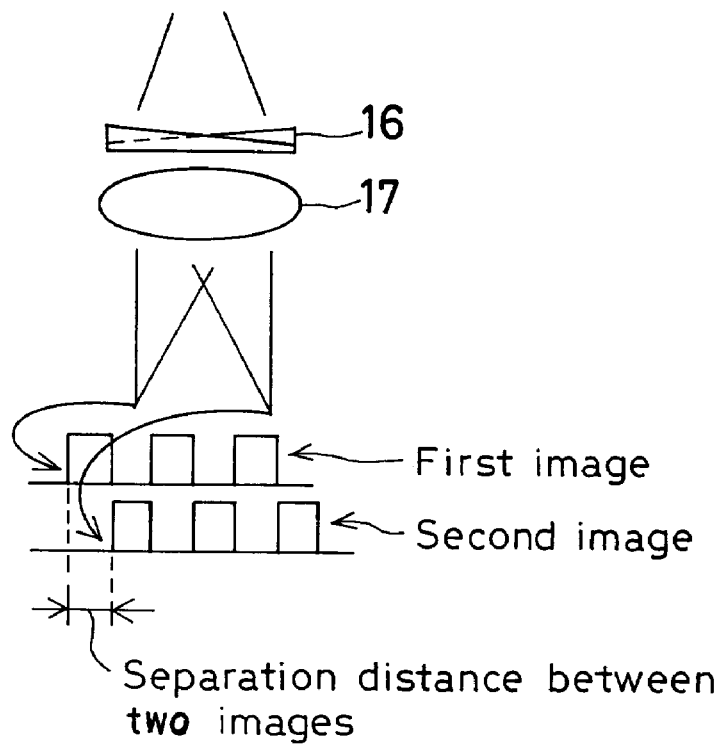

FIG.11(a)
FIG.11(b)
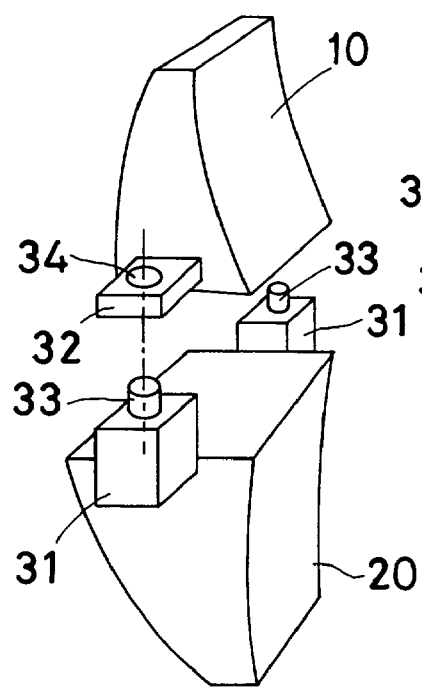
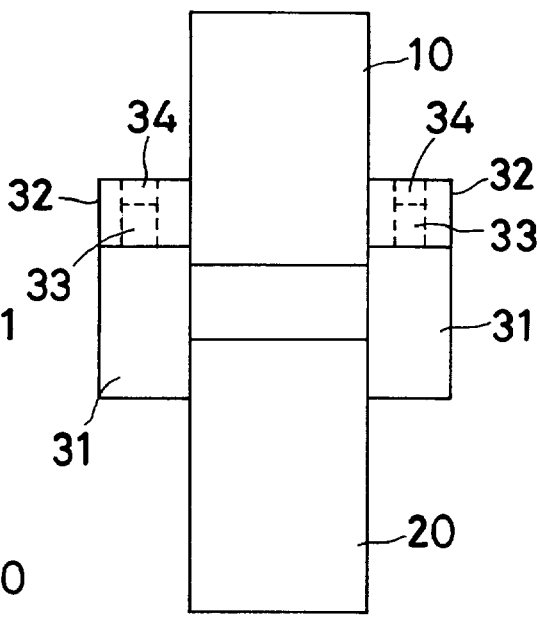
FIG. 12
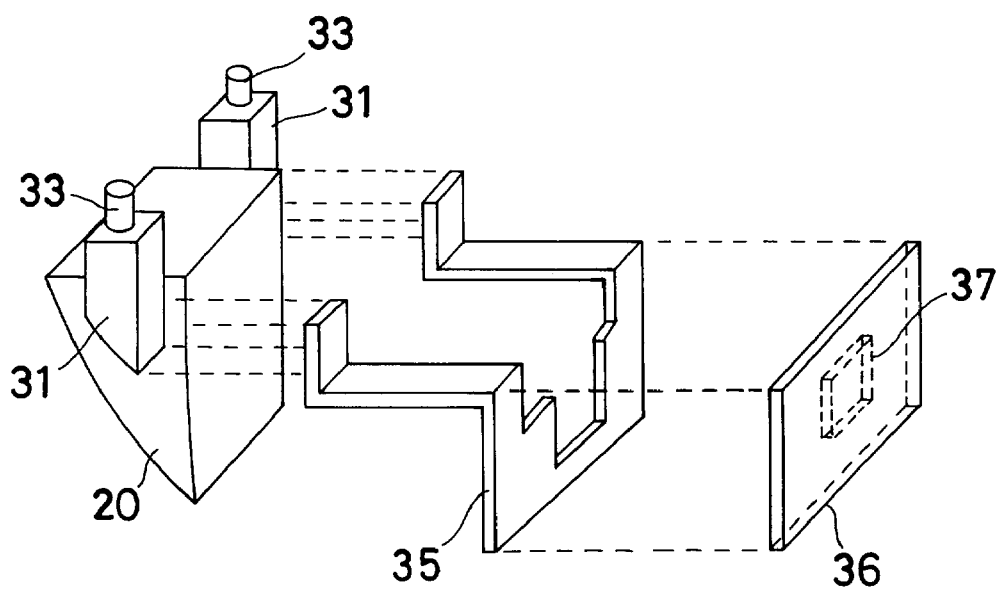

IMAGE-FORMING OPTICAL SYSTEM AND APPARATUS USING THE SAME

BACKGROUND OF THE INVENTION

The present invention relates to an image-forming optical system using an optical low-pass filter and also relates to an apparatus using the image-forming optical system. More particularly, the present invention relates to an image-forming optical system using an optical low-pass filter, which is suitable for use in digital still cameras, video cameras, endoscopes and so forth, which use a solid-state image pickup device, e.g. a CCD. The present invention also relates to an apparatus using such an image-forming optical system.

In recent years, a great variety of small-sized image pickup apparatus using a solid-state image pickup device, e.g. a CCD, have been commercially manufactured as represented by digital still cameras. Solid-state image pickup devices used in these apparatus are arranged to obtain desired image information concerning a subject by spatial sampling.

In general, solid-state image pickup devices have a discrete pixel structure. Therefore, if the subject contains a spatial frequency component higher than the sampling frequency, the solid-state image pickup device may generate a false signal, which is not originated from the subject, e.g. moire fringes, and also cause a beat phenomenon in which a fine fringe pattern becomes a thick fringe pattern having undulations in density. In addition, a false color may be produced. To minimize the influence of these undesired phenomena in an image pickup apparatus that uses a solid-state image pickup device, e.g. a CCD, an optical low-pass filter is placed in the optical system to limit high spatial frequency components of the subject that enter the solid-state image pickup device.

Generally known conventional optical low-pass filters are a low-pass filter that utilizes the birefringence of a uniaxial crystal such as quartz crystal, and a phase type low-pass filter that utilizes the diffraction phenomenon.

In the case of a quartz crystal filter, rays are separated by utilizing birefringence. Therefore, the amount of separation of rays depends on the thickness of the filter. Meanwhile, a necessary amount of ray separation is determined by the pixel pitch. Therefore, even if the size of the solid-state image pickup device reduces, the size of the quartz crystal filter does not change unless the pixel pitch changes. For this reason, it is difficult to apply the quartz crystal filter to optical apparatus that are required to be compact in size. Moreover, the quartz crystal filter is costly and hence makes it difficult to achieve a low-cost optical apparatus.

On the other hand, the phase type low-pass filter can be produced simply by forming a diffraction grating or the like on a substrate. In addition, the amount of ray separation depends on the pitch of the diffraction grating. Therefore, it is possible to achieve a thin low-pass filter. Furthermore, if a plastic or other similar material is used as a substrate, it is also possible to reduce the cost.

In general, the quartz crystal filter is placed between a solid-state image pickup device and an optical system that is telecentric on the image side, in order to obtain a necessary amount of separation of rays on the image plane. On the other hand, it is desirable for the phase type low-pass filter to be placed in the vicinity of the pupil of the optical system from the viewpoint of obtaining the low-pass filter effect substantially uniformly for the axial and extra-axial rays. Thus, the phase type low-pass filter can be placed inside the optical system, and it is possible to reduce the size of the optical system. There have heretofore been made a large number of propositions concerning the structure of optical low-pass filters, particularly phase type low-pass filters. However, there has been proposed no effective arrangement for achieving a compact optical system using such a low-pass filter structure.

There have also been proposed a large number of techniques wherein a reflecting surface is used for the purpose of reducing the thickness and size of an optical system using an optical low-pass filter [for example, see Japanese Patent Application Unexamined Publication (KOKAI) Nos. 8-292368 and 8-292371]. However, there is no prior art in which a thin and compact optical system is achieved by positively considering the arrangement and placement of an optical low-pass filter.

SUMMARY OF THE INVENTION

In view of the above-described problems associated with the prior art, an object of the present invention is to provide a compact, thin and low-cost image-forming optical system having an optical low-pass filter and also provide an apparatus using the image-forming optical system.

To attain the above-described object, the present invention provides an image-forming optical system for forming an image of an object. The image-forming optical system includes a stop and an object-side reflecting surface placed closer to the object side than the stop. The image-forming optical system further includes an image-side reflecting surface placed closer to the image side than the stop. Both the object-side reflecting surface and the image-side reflecting surface are formed from aspherical surfaces that give a power to a light beam when reflecting it. A low-pass filter for cutting off a high-frequency component is provided between the object-side reflecting surface and the image-side reflecting surface.

In addition, the present invention provides an image-forming optical system for forming an image of an object. The image-forming optical system includes a stop and a first prism placed closer to the object side than the stop. The image-forming optical system further includes a second prism placed closer to the image side than the stop. The first prism has an object-side reflecting surface with an aspherical surface configuration that reflects a light beam in the first prism and gives a power to the light beam when reflecting it. The second prism has an image-side reflecting surface with an aspherical surface configuration that reflects a light beam in the second prism and gives a power to the light beam when reflecting it. A low-pass filter for cutting off a high-frequency component is provided between the object-side reflecting surface and the image-side reflecting surface.

The reasons for adopting the above-described arrangements in the present invention, together with the functions thereof, will be described below.

The image-forming optical system according to the present invention is an optical system having reflecting surfaces in front of and behind a stop, in which a low-pass filter is placed in the vicinity of the stop. In a general coaxial optical system, optical elements are placed in series in the direction of the optical axis. Therefore, it is difficult to reduce the thickness in the direction of the optical axis. It is possible to somewhat reduce the thickness of such a coaxial optical system by selecting a thin type of optical system and increasing the power of each optical element. However, this cannot be regarded as a drastic solution to the problems. One approach to achieve a thin optical system is to introduce a reflecting surface to thereby fold the optical axis of the coaxial optical system.

Assuming that the direction of the optical axis of a coaxial optical system is a Z-axis, if only one reflecting surface is introduced, it is possible to reduce the thickness in the Z-axis direction but impossible to reduce the size in the direction of a Y-axis or X-axis. Therefore, the present invention adopts an arrangement in which reflecting surfaces are provided in front of and behind the stop, thereby folding the optical axis at least twice and thus attaining a thin and compact optical system. It is conceivable to introduce reflecting surfaces into the optical system at only one side of the stop, that is, only the object or image side of the stop. However, if a plurality of reflecting surfaces are introduced at only one side of the stop, the optical path length on the side where the reflecting surfaces are introduced increases because of the need to ensure a space for the reflecting surfaces, resulting in an optical system having an unbalanced optical path length with respect to the stop. Consequently, it becomes difficult to effect aberration correction, and the optical system itself becomes unfavorably large in size. Therefore, the present invention adopts an arrangement in which reflecting surfaces are provided in front of and behind the stop, as stated above, thereby making it possible to ensure favorable performance while keeping the optical system compact in size. Regarding the direction of reflection, because the direction in which the optical system can be made compact differs according to the type of optical system, at least one reflecting surface is arranged to reflect light in a direction in which the thickness in the Z-axis direction can be reduced. Other reflecting surfaces may be arranged to reflect light in any direction, i.e. the X-axis direction, the Y-axis direction, the Z-axis direction, or an oblique direction.

In an image-forming optical system using a solid-state image pickup device or the like that needs an optical low-pass filter, the power distribution depends largely on the installation position of the optical low-pass filter in the optical system. In particular, in a case where an optical low-pass filter that needs a thickness, such as a quartz crystal filter, is placed between the optical system and the image pickup device, it is necessary to adopt a retrofocus type power distribution in order to ensure a space for the optical low-pass filter and hence necessary to ensure a sufficiently long back focus. Consequently, the optical system becomes unavoidably large in size. At the same time, performance degradation due to the asymmetric power distribution occurs unavoidably.

In the optical system according to the present invention, a reduction in thickness in the Z-axis direction is attained by using reflecting surfaces, as stated above. Therefore, it is unnecessary to achieve a reduction in thickness in the Z-axis direction by only increasing the power of each optical element as in the conventional coaxial optical systems using no reflecting surface. Accordingly, it is possible to place an optical low-pass filter in a space provided near the stop. Consequently, it becomes unnecessary to ensure an excessively long back focus, and the asymmetry of the power distribution in the optical system is eased. Accordingly, it is possible to prevent performance degradation and upsizing due to the asymmetric power distribution. Thus, the above-described object of the present invention is attained.

The reflecting surfaces used in the present invention can utilize front-surface reflection using a mirror, back-surface reflection using a prism, and so forth. In the case of front-surface reflection using a mirror, no chromatic aberration occurs in theory. Therefore, there is no adverse effect on the performance of the optical system. In the case of back-surface reflection using a prism, the degree of freedom for aberration correction is increased by giving a curvature to each of the entrance and exit surfaces, and thus even more favorable performance can be attained. In particular, when a prism is used as a reflecting surface, because the positional relationship between the surfaces of the prism is fixed, it is only necessary to effect decentration control for the prism as a single unit, and there is no need for high assembly accuracy and a large number of man-hours for adjustment as are needed for ordinary reflecting surfaces, which have high sensitivity to decentration errors in comparison to refracting surfaces.

In the present invention, each reflecting surface itself can be provided with a power by giving a curvature thereto. In the case of a prism in particular, if the reflecting surface is assigned the greater part of the desired power to thereby reduce the powers of the entrance and exit surfaces, which are refracting surfaces, it is possible to reduce chromatic aberration to a very small quantity in comparison to refracting optical elements such as lenses while maintaining the degree of freedom for aberration correction at a high level in comparison to mirrors. Furthermore, the inside of a prism is filled with a transparent medium having a refractive index higher than that of air. Therefore, it is possible to obtain a longer optical path length than in the case of air. Accordingly, the use of a prism makes it possible to obtain an optical system that is thinner and more compact than those formed from lenses, mirrors and so forth, which are placed in the air.

Therefore, if the reflecting surface at each of the front and back sides of the stop in the present invention is arranged to utilize back-surface reflection by a prism and provided with a power, it is possible to reduce the number of constituent optical elements and also reduce the thickness and size of the optical system. At the same time, it is possible to maintain a satisfactory symmetry with respect to the stop and hence possible to favorably correct not only axial aberrations but also off-axis aberrations.

In the present invention, when a light ray from the object center that passes through the center of the stop and reaches the center of the image plane is defined as an axial principal ray, it is desirable that at least one of the reflecting surfaces should be decentered with respect to the axial principal ray. If at least one reflecting surface is not decentered with respect to the axial principal ray, the axial principal ray travels along the same optical path when incident on and reflected from the reflecting surface, and thus the axial principal ray is intercepted in the optical system undesirably. As a result, an image is formed from only a light beam whose central portion is shaded. Consequently, the center of the image is unfavorably dark, or no image is formed in the center of the image field.

It is also possible to decenter a reflecting surface with a power with respect to the axial principal ray. When a reflecting surface with a power is decentered with respect to the axial principal ray, it is desirable that at least one of the surfaces used in the present invention should be a rotationally asymmetric surface. It is particularly preferable from the viewpoint of aberration correction that at least one reflecting surface should be a rotationally asymmetric surface.

The reason for this will be described below in detail.

First, a coordinate system used in the following description and rotationally asymmetric surfaces will be described.

An optical axis defined by a straight line along which the axial principal ray travels until it intersects the first surface of the optical system is defined as a Z-axis. An axis perpendicularly intersecting the Z-axis in the decentration plane of each surface constituting the image-forming optical system is defined as a Y-axis. An axis perpendicularly intersecting the optical axis and also perpendicularly intersecting the Y-axis is defined as an X-axis. Ray tracing is forward ray tracing in which rays are traced from the object toward the image plane.

In general, a spherical lens system comprising only a spherical lens is arranged such that aberrations produced by spherical surfaces, such as spherical aberration, coma, and curvature of field, are corrected with some surfaces by canceling the aberrations with each other, thereby reducing aberrations as a whole.

On the other hand, rotationally symmetric aspherical surfaces and the like are used to correct aberrations favorably with a minimal number of surfaces. The reason for this is to reduce various aberrations that would be produced by spherical surfaces.

However, in a decentered optical system, rotationally asymmetric aberrations due to decentration cannot be corrected by a rotationally symmetric optical system. Rotationally asymmetric aberrations due to decentration include distortion, curvature of field, and astigmatic and comatic aberrations, which occur even on the axis.

First, rotationally asymmetric curvature of field will be described. For example, when rays from an infinitely distant object point are incident on a decentered concave mirror, the rays are reflected by the concave mirror to form an image. In this case, the back focal length from that portion of the concave mirror on which the rays strike to the image surface is a half the radius of curvature of the portion on which the rays strike in a case where the medium on the image side is air. Consequently, as shown in FIG. 20, an image surface tilted with respect to the axial principal ray is formed. It is impossible to correct such rotationally asymmetric curvature of field by a rotationally symmetric optical system.

To correct the tilted curvature of field by the concave mirror M itself, which is the source of the curvature of field, the concave mirror M is formed from a rotationally asymmetric surface, and, in this example, the concave mirror M is arranged such that the curvature is made strong (refracting power is increased) in the positive direction of the Y-axis, whereas the curvature is made weak (refracting power is reduced) in the negative direction of the Y-axis. By doing so, the tilted curvature of field can be corrected. It is also possible to obtain a flat image surface with a minimal number of constituent surfaces by placing a rotationally asymmetric surface having the same effect as that of the above-described arrangement in the optical system separately from the concave mirror M.

It is preferable that the rotationally asymmetric surface should be a rotationally asymmetric surface having no axis of rotational symmetry in the surface nor out of the surface. If the rotationally asymmetric surface has no axis of rotational symmetry in the surface nor out of the surface, the degree of freedom increases, and this is favorable for aberration correction.

Next, rotationally asymmetric astigmatism will be described.

A decentered concave mirror M produces astigmatism even for axial rays, as shown in FIG. 21, as in the case of the above. The astigmatism can be corrected by appropriately changing the curvatures in the X- and Y-axis directions of the rotationally asymmetric surface as in the case of the above.

Rotationally asymmetric coma will be described below.

A decentered concave mirror M produces coma even for axial rays, as shown in FIG. 22, as in the case of the above. The coma can be corrected by changing the tilt of the rotationally asymmetric surface according as the distance from the origin of the X-axis increases, and further appropriately changing the tilt of the surface according to the sign (positive or negative) of the Y-axis.

The image-forming optical system according to the present invention may also be arranged such that the above-described at least one surface having a reflecting action is decentered with respect to the axial principal ray and has a rotationally asymmetric surface configuration and further has a power. By adopting such an arrangement, decentration aberrations produced as the result of giving a power to the reflecting surface can be corrected by the surface itself. In addition, the power of the refracting surfaces of the prism is reduced, and thus chromatic aberration produced in the prism can be minimized.

The rotationally asymmetric surface used in the present invention should preferably be a plane-symmetry free-form surface having only one plane of symmetry. Free-form surfaces used in the present invention are defined by the following equation (a). It should be noted that the Z-axis of the defining equation is the axis of a free-form surface.

$$Z = cr^2 / \left[ 1 + \sqrt{\{1 - (1+k)c^2 r^2\}} \right] + \sum_{j=2}^{66} C_j X^m Y^n \quad (a)$$

In Eq. (a), the first term is a spherical surface term, and the second term is a free-form surface term.

In the spherical surface term:
c: the curvature at the vertex
k: a conic constant $$r = \sqrt{(X^2 + Y^2)}$$

The free-form surface term is given by $$\sum_{j=2}^{66} C_j X^m Y^n = C_2 X + C_3 Y + C_4 X^2 + C_5 XY + C_6 Y^2 + C_7 X^3 +$$
$$C_8 X^2 Y + C_9 X Y^2 + C_{10} Y^3 + C_{11} X^4 + C_{12} X^3 Y + C_{13} X^2 Y^2 +$$
$$C_{14} X Y^3 + C_{15} Y^4 + C_{16} X^5 + C_{17} X^4 Y + C_{18} X^3 Y^2 + C_{19} X^2 Y^3 +$$
$$C_{20} X Y^4 + C_{21} Y^5 + C_{22} X^6 + C_{23} X^5 Y + C_{24} X^4 Y^2 + C_{25} X^3 Y^3 +$$
$$C_{26} X^2 Y^4 + C_{27} X Y^5 + C_{28} Y^6 + C_{29} X^7 + C_{30} X^6 Y + C_{31} X^5 Y^2 +$$
$$C_{32} X^4 Y^3 + C_{33} X^3 Y^4 + C_{34} X^2 Y^5 + C_{35} X Y^6 + C_{36} Y^7 \ldots$$

where $C_j$ (j is an integer of 2 or higher) are coefficients.

In general, the above-described free-form surface does not have planes of symmetry in both the XZ- and YZ-planes. In the present invention, however, a free-form surface having only one plane of symmetry parallel to the YZ-plane is obtained by making all terms with odd-numbered powers of X zero. For example, in the above defining equation (a), the coefficients of the terms $C_2$, $C_5$, $C_7$, $C_9$, $C_{12}$, $C_{14}$, $C_{16}$, $C_{18}$, $C_{20}$, $C_{23}$, $C_{25}$, $C_{27}$, $C_{29}$, $C_{31}$, $C_{33}$, $C_{35}$, . . . are set equal to zero. By doing so, it is possible to obtain a free-form surface having only one plane of symmetry parallel to the YZ-plane.

A free-form surface having only one plane of symmetry parallel to the XZ-plane is obtained by making all terms with odd-numbered powers of Y zero. For example, in the above defining equation (a), the coefficients of the terms $C_3$, $C_5$, $C_8$, $C_{10}$, $C_{12}$, $C_{14}$, $C_{17}$, $C_{19}$, $C_{21}$, $C_{23}$, $C_{25}$, $C_{27}$, $C_{30}$, $C_{32}$, $C_{34}$, $C_{36}$, . . . are set equal to zero. By doing so, it is possible to obtain a free-form surface having only one plane of symmetry parallel to the XZ-plane.

Furthermore, the direction of decentration is determined in correspondence to either of the directions of the above-described planes of symmetry. For example, with respect to the plane of symmetry parallel to the YZ-plane, the direction of decentration of the optical system is determined to be the Y-axis direction. With respect to the plane of symmetry parallel to the XZ-plane, the direction of decentration of the optical system is determined to be the X-axis direction. By doing so, rotationally asymmetric aberrations due to decentration can be corrected effectively, and at the same time, the productivity can be improved.

It should be noted that the above defining equation (a) is shown as merely an example, and that the feature of the present invention resides in that rotationally asymmetric aberrations due to decentration are corrected and, at the same time, the productivity is improved by using a rotationally asymmetric surface having only one plane of symmetry. Therefore, the same advantageous effect can be obtained for any other defining equation that expresses such a rotationally asymmetric surface.

Furthermore, at least one prism used in the present invention should preferably have at least one optical surface having both reflecting and transmitting actions. This arrangement makes it possible to use a limited space effectively and to attain a reduction in size of the prism. In this case, the optical path length of rays passing through the prism is shortened. Consequently, it becomes possible to minimize the adverse effect produced by the transfer of decentration errors of reflecting surfaces, which have a high decentration error sensitivity. Accordingly, it is possible to ease the manufacturing accuracy required for the reflecting surfaces and hence possible to reduce the cost.

The reflecting action of the optical surface having both transmitting and reflecting actions should desirably be total reflection. If the condition for total reflection is not satisfied, the optical surface cannot have both reflecting and transmitting actions, and it becomes difficult to reduce the size of the prism. Furthermore, it is impossible to ease the manufacturing accuracy required for each reflecting surface.

Reflecting surfaces used in the present invention, exclusive of totally reflecting surfaces, are preferably formed from a reflecting surface having a thin film of a metal, e.g. aluminum or silver, formed on the surface thereof, or a reflecting surface formed from a dielectric multilayer film. In the case of a metal thin film having reflecting action, a high reflectivity can be readily obtained. The use of a dielectric reflecting film is advantageous in a case where a reflecting film having wavelength selectivity or minimal absorption is to be formed.

In the present invention, focusing of the image-forming optical system can be effected by moving all the constituent elements or moving only one prism. However, lit is also possible to effect focusing by moving the image-formation plane in the direction of the axial principal ray exiting from the surface closest to the image side. By doing so, it is possible to prevent displacement of the axial principal ray on the entrance side due to focusing even if the direction in which the axial principal ray from the object enters the optical system is not coincident with the direction of the axial principal ray exiting from the surface closest to the image side owing to the decentration of the image-forming optical system. It is also possible to effect focusing by using a focusing prism 6 as shown in FIG. 4. The focusing prism 6 has a plurality of wedge-shaped prisms P1 and P2 formed by dividing a plane-parallel plate. Focusing is effected by moving the wedge-shaped prisms P1 and P2 in a direction perpendicular to the Z-axis (optical axis). In this case also, focusing can be performed independently of the decentration of the image-forming optical system.

The optical low-pass filter used in the optical system according to the present invention may utilize the birefringence of quartz crystal or the like. Considering achievement of a thin optical system, however, it is preferable to use a phase type optical low-pass filter. A low-pass filter that utilize the birefringence of quartz crystal or the like needs a thickness corresponding to the pixel pitch because the amount of ray separation is determined by the thickness. In contrast, the amount of ray separation caused by a phase type optical low-pass filter does not depend on the thickness. Therefore, the use of a phase type optical low-pass filter makes it possible to achieve a thin optical system. In addition, because a phase type optical low-pass filter is placed in the vicinity of the stop, the same advantageous effect can be obtained for both the axial and extra-axial rays. Accordingly, a favorable optical arrangement can be obtained.

Examples of phase type optical low-pass filters preferable to use in the present invention are a diffraction grating type, a phase grating type as shown in the sectional view of FIG. 5, e.g. an arcuate grating type [part (a) of FIG. 5], a triangular grating type [part (b) of FIG. 5], a trapezoidal grating type [part (c) of FIG. 5], a sinusoidal grating type [part (d) of FIG. 5], or a rectangular grating type [part (e) of FIG. 5], and a split-image type [part (f) of FIG. 5; perspective view] that is formed from a combination of wedges. The use of one of these optical low-pass filters makes it possible to simultaneously attain a reduction in thickness and a reduction in size of the optical system while obtaining the desired advantageous effects.

FIG. 6 shows an example of an image pickup optical system of a television camera using an optical low-pass filter of the split-image type [part (f) of FIG. 5] among the above-described phase type optical low-pass filters. Part (a) of FIG. 6 shows the orientation of a single-sided polyhedral lens 16 that constitutes the optical low-pass filter. As shown in the figure, the single-sided polyhedral lens 16 is placed so that a boundary line (dividing line) 15 between two surface portions on one side of the single-sided polyhedral lens 16 lies in the horizontal direction, that is, in parallel to the horizontal (breadthwise) direction of a solid-state image pickup device 18. In this case, the image separates into two images in the horizontal scanning direction of the solid-state image pickup device 18. More specifically, part (b) of FIG. 6 shows a double image formed through the single-sided polyhedral lens 16. The two images are formed apart from each other in the horizontal direction by a distance d. It is assumed in the present invention that the horizontal (breadthwise) direction of the solid-state image pickup device 18 is set to the X-axis, and the vertical (lengthwise) direction to the Y-axis.

FIG. 7 is a diagram for explaining the function of removing moire fringes by forming a double image using the single-sided polyhedral lens 16 in the image pickup optical system. The basic idea of removing moire fringes is as follows: In sampling of an object image, if the sampling frequency is close to a frequency component contained in the object image, moire fringes appear. Therefore, the optical low-pass filter is set to frequency characteristics with which the relevant frequency component is removed.

As shown in FIG. 7, if an object which is bright and dark at a repeating period is imaged (on the image pickup surface of the solid-state image pickup device 18) through the single-sided polyhedral lens 16 and an image-forming lens 17, a first image is formed through one surface portion on one side of the single-sided polyhedral lens 16, and a second image is formed through the other surface portion. In a case where the distance by which the first and second images are apart from each other is set to ½ of the period, if the intensity distributions of the two images are superimposed on one another, the peaks of the intensity distribution of one image fill the troughs of the intensity distribution of the other image, resulting in uniform intensity distributions. Consequently, the presence of moire fringes is unrecognizable. In other words, if such a double image is formed, a frequency component having a repeating period which is double the separation distance between the two images disappears. Accordingly, moire fringes can be removed by properly setting the relationship between the pixel sampling pitch (repeating period) and the image separation distance.

It is also possible to form a diffraction grating or the like on a surface near the stop so that the surface functions as a phase type optical low-pass filter. By doing so, the number of components can be reduced, and thus the cost is reduced. FIG. 8 is a schematic perspective view showing an example of the above-described arrangement. In the example, the entrance surface 21 of the second prism 20 in the image-forming optical system according to the present invention is formed into a polyhedral configuration in which lines normal to a plurality surface portions are in a skew relation to each other with respect to an optical axis 1, and which has a low-pass function. Instead of the entrance surface 21 of the second prism 20, the exit surface of the first prism in the image-forming optical system according to the present invention may be formed into a similar polyhedral configuration.

Incidentally, it is known that the effect of the phase type optical low-pass filter weakens as the aperture is stopped down. This is due to the fact that the pitch of the phase grating or the like that gives the effect of the phase type optical low-pass filter to a light beam passing through it reduces as the aperture is stopped down. Accordingly, although the amount of light entering a solid-state image pickup device or the like can be limited by stopping down the aperture, it is also possible to use a method of limiting the amount of light without changing the effect of the phase type optical low-pass filter. That is, the amount of light may be limited directly by using an ND filter. Alternatively, the amount of light may be limited by changing the shutter speed with a liquid crystal shutter. It is also possible to limit the amount of light by varying the shutter speed using a solid-state image pickup device such as a progressive CCD.

In the present invention, if the phase type optical low-pass filter and the prisms are formed by using a resin material such as a plastic material, the cost can be reduced. It is desirable to use a material of low moisture absorption, such as amorphous polyolefin, because such a material has a minimum change in image-forming performance with changes in moisture.

Furthermore, as shown in FIG. 9, the optical path can be folded in a direction different from the decentration direction of the image-forming optical system according to the present invention by placing a reflecting member 7, e.g. a mirror, on the object side of the entrance surface of the image-forming optical system. By doing so, the degree of freedom for layout of the image-forming optical system further increases, and the overall size of the image-forming optical apparatus can be further reduced.

In the present invention, the image-forming optical system can be formed from prisms alone. A refracting optical element such as a lens suffers chromatic aberration occurring at an interface surface thereof and requires another refracting optical element to correct the chromatic aberration. A prism also has refracting surfaces as entrance and exit surfaces thereof. However, chromatic aberration can be reduced to a very small quantity by assigning the greater part of the desired power to a reflecting surface, which produces no chromatic aberration, and correspondingly reducing the power of each of the refracting surfaces. Thus, favorable chromatic aberration correction can be effected by a prism alone. However, by providing a plurality of prisms in front of and behind the stop to obtain a symmetry with respect to the stop as in the present invention, it is possible to favorably correct chromatic aberration, particularly lateral chromatic aberration, even when each individual prism is not completely corrected for chromatic aberration.

However, when a refracting optical element such as a lens is placed in the image-forming optical system according to the present invention, chromatic aberration occurs markedly in comparison to an arrangement formed from prisms alone. To correct the chromatic aberration, another refracting optical element must be added. As a result, the number of constituent optical elements increases, and the cost rises. In addition, the optical system itself becomes unfavorably large in size. Therefore, it is preferable from the viewpoint of chromatic aberration correction that the image-forming optical system should be formed from prisms alone. By doing so, it is possible to obtain a low-cost, high-performance and compact image-forming optical system that has a reduced umber of constituent optical elements in comparison to a refracting optical system.

As shown in FIG. 10, the arrangement may be such that the stop 2 is formed from a single aperture, and the optical low-pass filter 4 and a plurality of prisms 10 and 20 are integrated into one prism, with the stop 2 put therebetween. By doing so, the cost can be further reduced. It should be noted that the term "arrangement formed from prisms alone" used herein means that the image-forming optical system has only prisms as optical elements having a power, exclusive of optical elements having no power. Examples of optical elements equivalent to those which have no power include a filter that is placed in front of a photographic optical system.

In the present invention, the image-forming optical system should preferably be a single focal length lens system from the viewpoint of maintaining the required image-forming performance, although not limitative. It should be noted that when the image-forming optical system according to the present invention is arranged in the form of a zoom lens system, it is desirable to use a moving mechanism as stated in examples (described later).

In the present invention, it is desirable to satisfy the following condition:

$$1° < |\theta| << 90° \tag{1-1}$$

where $\theta$ is the angle formed between the axial principal ray and a line normal to a rotationally asymmetric surface having a reflecting action in the decentration direction at a point where the axial principal ray intersects the rotationally asymmetric surface.

By tilting a rotationally asymmetric surface with respect to the axial principal ray, correction of decentration aberrations can be performed effectively. In particular, when a decentered reflecting surface has a power, it is possible to correct comatic and astigmatic aberrations due to decentration.

If $|\theta|$ is not smaller than the upper limit of the condition (1-1), i.e. 90°, the amount of comatic and astigmatic aberrations due to decentration that are produced by this surface becomes excessively large, resulting in over-correction. Thus, it becomes difficult to correct decentration aberrations with good balance. If $|\theta|$ is not larger than the lower limit of the condition (1-1), i.e. 1°, it becomes impossible for this surface to correct comatic and astigmatic aberrations due to decentration that are produced by another surface, and the resolution degrades even for an axial image.

It is more desirable from the viewpoint of aberration correction to satisfy the following condition:

$$10° < |\theta| < 80° \qquad (1\text{-}2)$$

It is necessary for $|\theta|$ to be larger than the lower limit of this condition, i.e. 10°, in order to correct aberrations produced by another surface. If $|\theta|$ is not smaller than the upper limit, i.e. 80°, the amount of comatic and astigmatic aberrations due to decentration that are produced by this surface becomes excessively large, resulting in over-correction. Thus, it becomes difficult to correct decentration aberrations with good balance.

It is still more desirable to satisfy the following condition:

$$10° < |\theta| < 60° \qquad (1\text{-}3)$$

By satisfying the condition (1-3), the aberration correcting performance is further improved.

When a reflecting surface having a power has only a reflecting action, it is desirable to satisfy the following condition:

$$5° < |\Theta| < 45° \qquad (2\text{-}1)$$

where $\Theta$ is the angle formed between the axial principal ray and a line normal to the reflecting surface in the decentration direction at a point where the axial principal ray intersects the reflecting surface.

This is a condition provided to make it possible to minimize the amount of decentration aberrations produced from a reflecting surface having only a reflecting action even when the greater part of the desired power is assigned to the reflecting surface, while favorably reducing the thickness and size of the image-forming optical system. If $|\Theta|$ is not larger than the lower limit of the condition (2-1), i.e. 5°, the axial principal ray is undesirably reflected approximately in the Z-axis direction. Consequently, it becomes impossible to achieve a reduction in thickness of the optical system. If $|\Theta|$ is not smaller than the upper limit, i.e. 45°, the amount of decentration of the reflecting surface becomes excessively large. Consequently, it becomes impossible to correct satisfactorily decentration aberrations produced by the reflecting surface even if a rotationally asymmetric surface is used.

It is more desirable to satisfy the following condition:

$$10° < |\Theta| < 30° \qquad (2\text{-}2)$$

By satisfying the condition (2-2), it becomes possible to increase the power of the reflecting surface while minimizing the amount of decentration aberrations produced by the reflecting surface. Accordingly, it is possible to further reduce the thickness and size of the image-forming optical system.

In the present invention, the refracting and reflecting surfaces of the image-forming optical system may be formed from spherical surfaces or rotationally symmetric aspherical surfaces.

Still other objects and advantages of the invention will in part be obvious and will in part be apparent from the specification.

The invention accordingly comprises the features of construction, combinations of elements, and arrangement of parts which will be exemplified in the construction hereinafter set forth, and the scope of the invention will be indicated in the claims.

BRIEF DESCRIPTION OF THE DRAWINGS

FIG. 4 is a sectional view showing a modification that uses a prism for focusing.

FIG. 6 is a diagram for describing an image pickup optical system using a split image type optical low-pass filter.

FIG. 7 is a diagram for describing the operation of the image pickup optical system shown in FIG. 6.

FIG. 11 is a diagram showing one example of a mounting mechanism wherein two prisms of the image-forming optical system according to the present invention are united into an integral structure.

FIG. 12 is a perspective view showing an example of an arrangement in which a CCD is mechanically united with the integral structure shown in FIG. 11.

DESCRIPTION OF THE PREFERRED EMBODIMENTS

Figure 1:
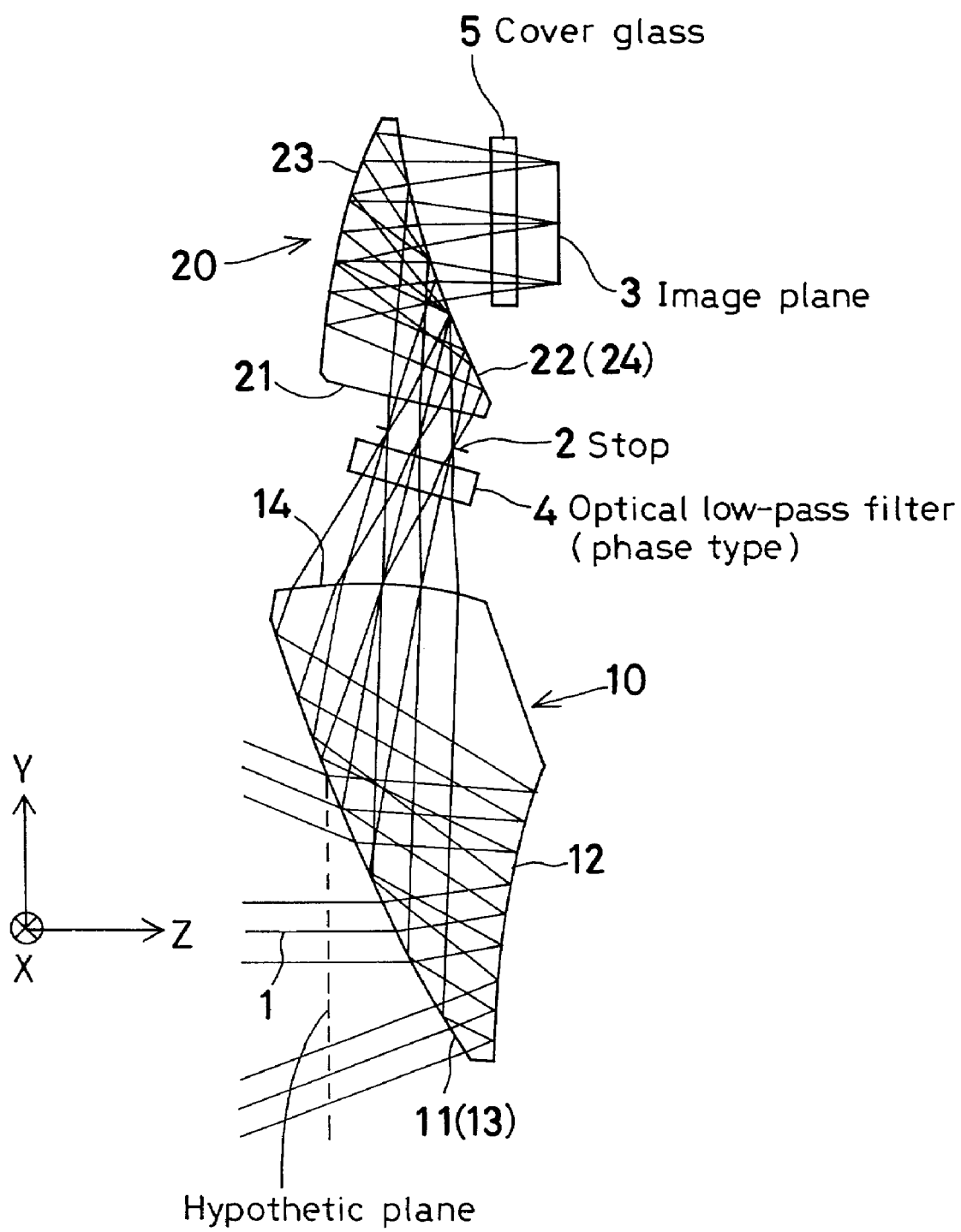
FIG. 1 is a sectional view of an image-forming optical system according to Example 1 of the present invention.

Example 1 of the image-forming optical system according to the present invention will be described below. It should be noted that constituent parameters of Example 1 will be shown later. In Example 1, as shown in FIG. 1, the center of a specific surface of the optical system (each of the hypothetic plane of surface No. 1 and the stop plane of surface No. 8) is defined as the origin of a decentered optical system, and an axial principal ray 1 is defined by a ray emanating from the center of an object and passing through the center of a stop 2. A Z-axis is taken in the direction in which the axial principal ray 1 travels from the object center to the first surface of the optical system. A plane containing the Z-axis and the center of the image plane is defined as a YZ-plane. A Y-axis is taken in a direction in the YZ-plane that perpendicularly intersects the Z-axis in a plane in which rays are folded by the surfaces of the optical system. The direction in which the Z-axis extends from the object point toward the first surface of the optical system is defined as a positive direction of the Z-axis. The upward direction as viewed in FIG. 1 is defined as a positive direction of the Y-axis. An axis that constitutes a right-handed orthogonal coordinate system in combination with the Y- and Z-axes is defined as an X-axis.

In Example 1, decentration of each surface is made in the YZ-plane, and the one and only plane of symmetry of each rotationally asymmetric free-form surface is the YZ-plane.

Regarding decentered surfaces, each surface is given displacements in the X-, Y- and Z-axis directions (X, Y and Z, respectively) of the vertex position of the surface from the origin of the optical system, and tilt angles (degrees) of the center axis of the surface [the Z-axis of the above equation (a) in regard to free-form surfaces; the Z-axis of the following equation (b) in the case of aspherical surfaces] with respect to the X-, Y- and Z-axes ($\alpha$, $\beta$, and $\gamma$, respectively). In this case, positive $\alpha$ and $\beta$ mean counterclockwise rotation relative to the positive directions of the corresponding axes, and positive $\gamma$ means clockwise rotation relative to the positive direction of the Z-axis.

Among optical surfaces constituting the optical system in Example 1, a specific surface and a surface subsequent thereto are given a surface separation when these surfaces form a coaxial optical system. In addition, the refractive index and Abbe's number of each medium are given according to the conventional method.

The configuration of each free-form surface used in the present invention is defined by the above equation (a). The Z-axis of the defining equation is the axis of the free-form surface.

Aspherical surfaces used in the present invention are rotationally symmetric aspherical surfaces given by the following equation:

$$Z = (y^2/R)/[1+\{1-(1+K)y^2/R^2\}^{1/2}] + Ay^4 + By^6 + Cy^8 + Dy^{10} + \quad \text{(b)}$$

In the above equation, Z is an optical axis (axial principal ray) for which the direction of travel of light is defined as a positive direction, and y is taken in a direction perpendicular to the optical axis. R is a paraxial curvature radius, K is a conic constant, and A, B, C, D ... are 4th-, 6th-, 8th- and 10th-order aspherical coefficients, respectively. The Z-axis of this defining equation is the axis of the rotationally symmetric aspherical surface.

In the constituent parameters (shown later), those terms concerning free-form surfaces and aspherical surfaces for which no data is shown are zero. The refractive index is expressed by the refractive index for the spectral d-line (wavelength: 587.56 nanometers). Lengths are given in millimeters.

Free-form surfaces may also be defined by Zernike polynomials. That is, the configuration of a free-form surface may be defined by the following equation (c). The Z-axis of the defining equation (c) is the axis of Zernike polynomial. A rotationally asymmetric surface is defined by polar coordinates of the height of the Z-axis with respect to the XY-plane. In the equation (c), A is the distance from the Z-axis in the XY-plane, and R is the azimuth angle about the Z-axis, which is expressed by the angle of rotation measured from the Z-axis.

$$x = R \times \cos(A) \qquad \text{(c)}$$

$$y = R \times \sin(A)$$

$$\begin{aligned}Z = &\ D_2 + D_3 R\cos(A) + D_4 R\sin(A) + D_5 R^2\cos(2A) + \\ &\ D_6(R^2 - 1) + D_7 R^2\sin(2A) + D_8 R^3\cos(3A) + \\ &\ D_9(3R^3 - 2R)\cos(A) + D_{10}(3R^3 - 2R)\sin(A) + \\ &\ D_{11} R^3\sin(3A) + D_{12} R^4\cos(4A) + D_{13}(4R^4 - 3R^2)\cos(2A) + \\ &\ D_{14}(6R^4 - 6R^2 + 1) + D_{15}(4R^4 - 3R^2)\sin(2A) + \\ &\ D_{16} R^4\sin(4A) + D_{17} R^5\cos(5A) + D_{18}(5R^5 - 4R^3)\cos(3A) + \\ &\ D_{19}(10R^5 - 12R^3 + 3R)\cos(A) + D_{20}(10R^5 - 12R^3 + 3R)\sin(A) + \\ &\ D_{21}(5R^5 - 4R^3)\sin(3A) + D_{22} R^5\sin(5A) + D_{23} R^6\cos(6A) + \\ &\ D_{24}(6R^6 - 5R^4)\cos(4A) + D_{25}(15R^6 - 20R^4 + 6R^2)\cos(2A) + \\ &\ D_{26}(20R^6 - 30R^4 + 12R^2 - 1) + \\ &\ D_{27}(15R^6 - 20R^4 + 6R^2)\sin(2A) + \\ &\ D_{28}(6R^6 - 5R^4)\sin(4A) + D_{29} R^6\sin(6A) \cdots\end{aligned}$$

In the above equation, to design an optical system symmetric with respect to the X-axis direction, $D_4$, $D_5$, $D_6$, $D_{10}$, $D_{11}$, $D_{12}$, $D_{13}$, $D_{14}$, $D_{20}$, $D_{21}$, $D_{22}$ should be used.

Other examples of surfaces usable in the present invention are expressed by the following defining equation (d):

$$Z = \Sigma\Sigma C_{nm} XY$$

Assuming that k=7 (polynomial of degree 7), for example, a free-form surface is expressed by an expanded form of the above equation as follows:

$$\begin{aligned}Z = &\ C_2 + C_3 y + C_4|x| + C_5 y^2 + C_6 y|x| + C_7 x^2 + C_8 y^3 + C_9 y^2|x| + \quad \text{(d)}\\ &\ C_{10} yx^2 + C_{11}|x^3| + C_{12} y^4 + C_{13} y^3|x| + C_{14} y^2 x^2 + C_{15} y|x^3| + \\ &\ C_{16} x^4 + C_{17} y^5 + C_{18} y^4|x| + C_{19} y^3 x^2 + C_{20} y^2|x^3| + C_{21} yx^4 + \\ &\ C_{22}|x^5| + C_{23} y^6 + C_{24} y^5|x| + C_{25} y^4 x^2 + C_{26} y^3|x^3| + \\ &\ C_{27} y^2 x^4 + C_{28} y|x^5| + C_{29} x^6 + C_{30} y^7 + C_{31} y^6|x| + C_{32} y^5 x^2 + \\ &\ C_{33} y^4|x^3| + C_{34} y^3 x^4 + C_{35} y^2|x^5| + C_{36} yx^6 + C_{37}|x^7|\end{aligned}$$

Although in the examples of the present invention the surface configuration is expressed by a free-form surface using the above equation (a), it should be noted that the same advantageous effect can be obtained by using the above equation (c) or (d).

In Example 1, it is assumed that an image pickup device of ⅓ inch size in which the image size is about 2.5×1.8 millimeters is used. It should be noted that the present invention is also applicable to image pickup devices of other sizes. The present invention includes not only an image pickup optical system using the image-forming optical system according to the present invention but also an image pickup apparatus incorporating the optical system.

Figure 2:
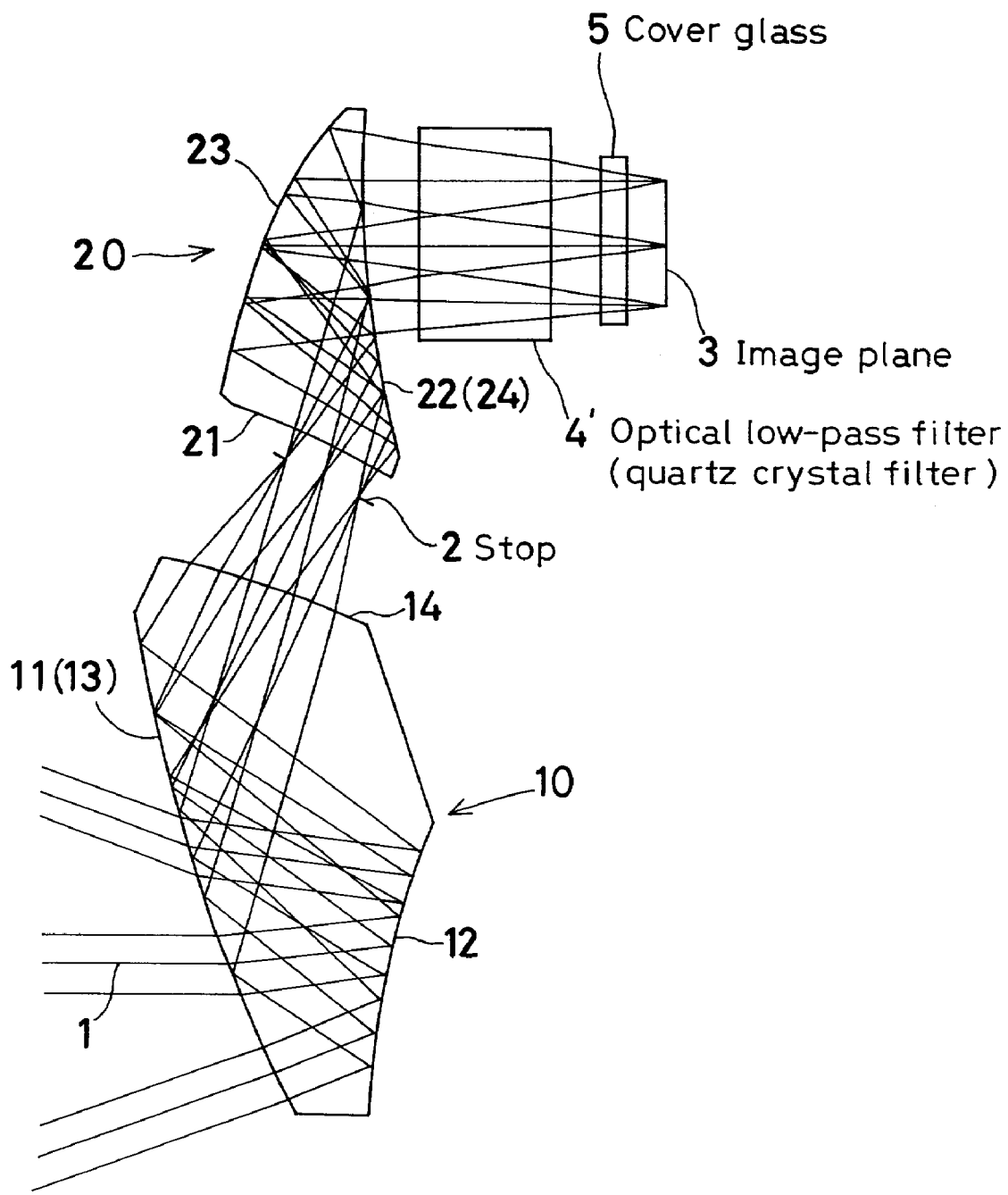
FIG. 2 is a sectional view of a comparative example that uses a quartz crystal type low-pass filter.

FIG. 1 is a sectional view of Example 1 taken along the YZ-plane containing the axial principal ray. It should be noted that FIG. 2 is a similar sectional view showing a comparative example in the same scale. In the comparative example (illustrated only by the drawing), a quartz crystal type low-pass filter 4' is provided between the second prism 20 and the image plane 3. It will be clear that the present invention has attained a reduction in thickness in the Z-axis direction. In Example 1, the horizontal half field angle is 26.1 degrees, and the vertical half field angle is 20.2 degrees. The entrance pupil diameter is 1.78 millimeters. The image pickup device size is 2.45×1.84 millimeters. The focal length is equivalent to 5 millimeters in terms of the focal length of a rotationally symmetric optical system. Example 1 has, in order in which light passes from the object side, a first prism 10, a phase type optical low-pass filter 4, a stop 2, a second prism 20, a cover glass 5 for protecting the imager surface, and an image plane (imager light-receiving surface) 3. The first prism 10 has a first transmitting surface 11 of positive power, a first reflecting surface 12 of negative power, a second reflecting surface 13 of positive power, and a second transmitting surface 14 of positive power. The second prism 20 has a first transmitting surface 21 of positive power, a first reflecting surface 22 of negative power, a second reflecting surface 23 of positive power, and a second transmitting surface 24 of negative power. The first transmitting surface 11 and second reflecting surface 13 of the first prism 10 are the identical optical surface having both transmitting and reflecting actions, and the first reflecting surface 22 and second transmitting surface 24 of the second prism 20 are the identical optical surface having both transmitting and reflecting actions.

In the constituent parameters (shown below), the displacements of each of the surface Nos. 2 to 6 are expressed by the amounts of displacement from the decentration reference plane 1, and the displacements of each of the surface Nos. 9 to 13 are expressed by the amounts of displacement from the decentration reference plane 2. The image plane 3 is perpendicular to the Z-axis.

Constituent parameters of the above-described Example 1 will be shown below. In the constituent parameters, free-form surfaces are denoted by "FFS", and rotationally symmetric aspherical surfaces by "ASS". "HRP" denotes a hypothetic plane.

EXAMPLE 1

| Surface No. | Radius of curvature | Surface separation | Displacement and tilt | Refractive index | Abbe's No. |
|---|---|---|---|---|---|
| Object plane | ∞ | ∞ | | | |
| 1 | ∞ (HRP) | | | (Reference plane 1) | |
| 2 | FFS① | | (1) | 1.4924 | 57.6 |
| 3 | FFS② (Reflection surface) | | (2) | 1.4924 | 57.6 |
| 4 | FFS① (Reflection surface) | | (1) | 1.4924 | 57.6 |
| 5 | ASS① | | (3) | | |
| 6 | ∞ | 1.00 | (4) | 1.4924 | 57.6 |
| 7 | ∞ (Optical low-pass filter) | 0.50 | | | |
| 8 | ∞ (Stop) | | | (Reference plane 2) | |
| 9 | ASS② | | (5) | 1.4924 | 57.6 |
| 10 | FFS③ (Reflection surface) | | (6) | 1.4924 | 57.6 |
| 11 | FFS④ (Reflection surface) | | (7) | 1.4924 | 57.6 |
| 12 | FFS③ | | (6) | | |
| 13 | ∞ | 0.75 | (8) | 1.4875 | 70.2 |
| 14 | ∞ (Cover glass) | 1.21 | | | |
| Image plane | ∞ | | | | |

ASS①

R   −9.69
K   0.0000
A   $5.7365 \times 10^{-4}$
B   $-6.2259 \times 10^{-6}$
C   $9.9952 \times 10^{-8}$
D   $-6.7329 \times 10^{-10}$

ASS②

R   241.31
K   0.0000
A   $-5.8239 \times 10^{-4}$
B   $1.3867 \times 10^{-4}$
C   $-9.4417 \times 10^{-6}$
D   $2.5524 \times 10^{-7}$

FFS①

| $C_4$ | $7.9105 \times 10^{-3}$ | $C_6$ | $5.8456 \times 10^{-3}$ | $C_8$ | $-8.2836 \times 10^{-6}$ |
| $C_{10}$ | $-1.7361 \times 10^{-4}$ | $C_{11}$ | $-2.5521 \times 10^{-6}$ | $C_{13}$ | $-2.2102 \times 10^{-5}$ |
| $C_{15}$ | $1.3676 \times 10^{-5}$ | $C_{17}$ | $4.7297 \times 10^{-6}$ | $C_{19}$ | $-5.5491 \times 10^{-7}$ |
| $C_{21}$ | $-1.0642 \times 10^{-6}$ | | | | |

FFS②

| $C_4$ | $1.1670 \times 10^{-2}$ | $C_6$ | $1.5926 \times 10^{-2}$ | $C_8$ | $-6.3243 \times 10^{-5}$ |
| $C_{10}$ | $-8.1559 \times 10^{-4}$ | $C_{11}$ | $3.2830 \times 10^{-6}$ | $C_{13}$ | $-2.6658 \times 10^{-5}$ |
| $C_{15}$ | $1.6086 \times 10^{-4}$ | $C_{17}$ | $6.2610 \times 10^{-6}$ | $C_{19}$ | $6.8933 \times 10^{-7}$ |
| $C_{21}$ | $-1.4004 \times 10^{-5}$ | | | | |

FFS③

| $C_4$ | $1.4319 \times 10^{-2}$ | $C_6$ | $6.6299 \times 10^{-3}$ | $C_8$ | $-8.7012 \times 10^{-5}$ |
| $C_{10}$ | $3.5430 \times 10^{-4}$ | $C_{11}$ | $2.2861 \times 10^{-5}$ | $C_{13}$ | $4.0481 \times 10^{-5}$ |
| $C_{15}$ | $1.1692 \times 10^{-4}$ | $C_{17}$ | $2.3745 \times 10^{-5}$ | $C_{19}$ | $-2.3469 \times 10^{-5}$ |
| $C_{21}$ | $-7.4046 \times 10^{-6}$ | | | | |

FFS④

| $C_4$ | $3.4614 \times 10^{-2}$ | $C_6$ | $2.9441 \times 10^{-2}$ | $C_8$ | $2.6927 \times 10^{-4}$ |
| $C_{10}$ | $6.4034 \times 10^{-4}$ | $C_{11}$ | $4.4102 \times 10^{-5}$ | $C_{13}$ | $9.9462 \times 10^{-6}$ |
| $C_{15}$ | $2.5689 \times 10^{-4}$ | $C_{17}$ | $8.8311 \times 10^{-6}$ | $C_{19}$ | $-1.6809 \times 10^{-7}$ |
| $C_{21}$ | $2.1963 \times 10^{-5}$ | | | | |

Displacement and tilt (1)

| X | 0.00 | Y | 3.75 | Z | 0.50 |
| α | 23.90 | β | 0.00 | γ | 0.00 |

Displacement and tilt (2)

| X | 0.00 | Y | 0.56 | Z | 5.62 |
| α | −11.23 | β | 0.00 | γ | 0.00 |

Displacement and tilt (3)

| X | 0.00 | Y | 10.10 | Z | 3.87 |
| α | 77.63 | β | 0.00 | γ | 0.00 |

Displacement and tilt (4)

| X | 0.00 | Y | 13.24 | Z | 2.47 |
| α | 74.91 | β | 0.00 | γ | 0.00 |

Displacement and tilt (5)

-continued

|   |        |   |       |   |      |
|---|--------|---|-------|---|------|
| X | 0.00   | Y | −1.92 | Z | 1.18 |
| α | 4.42   | β | 0.00  | γ | 0.00 |
| Displacement and tilt (6) | | | | | |
| X | 0.00   | Y | 0.07  | Z | 3.91 |
| α | −53.98 | β | 0.00  | γ | 0.00 |
| Displacement and tilt (7) | | | | | |
| X | 0.00   | Y | 4.09  | Z | 5.31 |
| α | −89.11 | β | 0.00  | γ | 0.00 |
| Displacement and tilt (8) | | | | | |
| X | 0.00   | Y | −0.42 | Z | 6.81 |
| α | −74.91 | β | 0.00  | γ | 0.00 |

Figure 3:
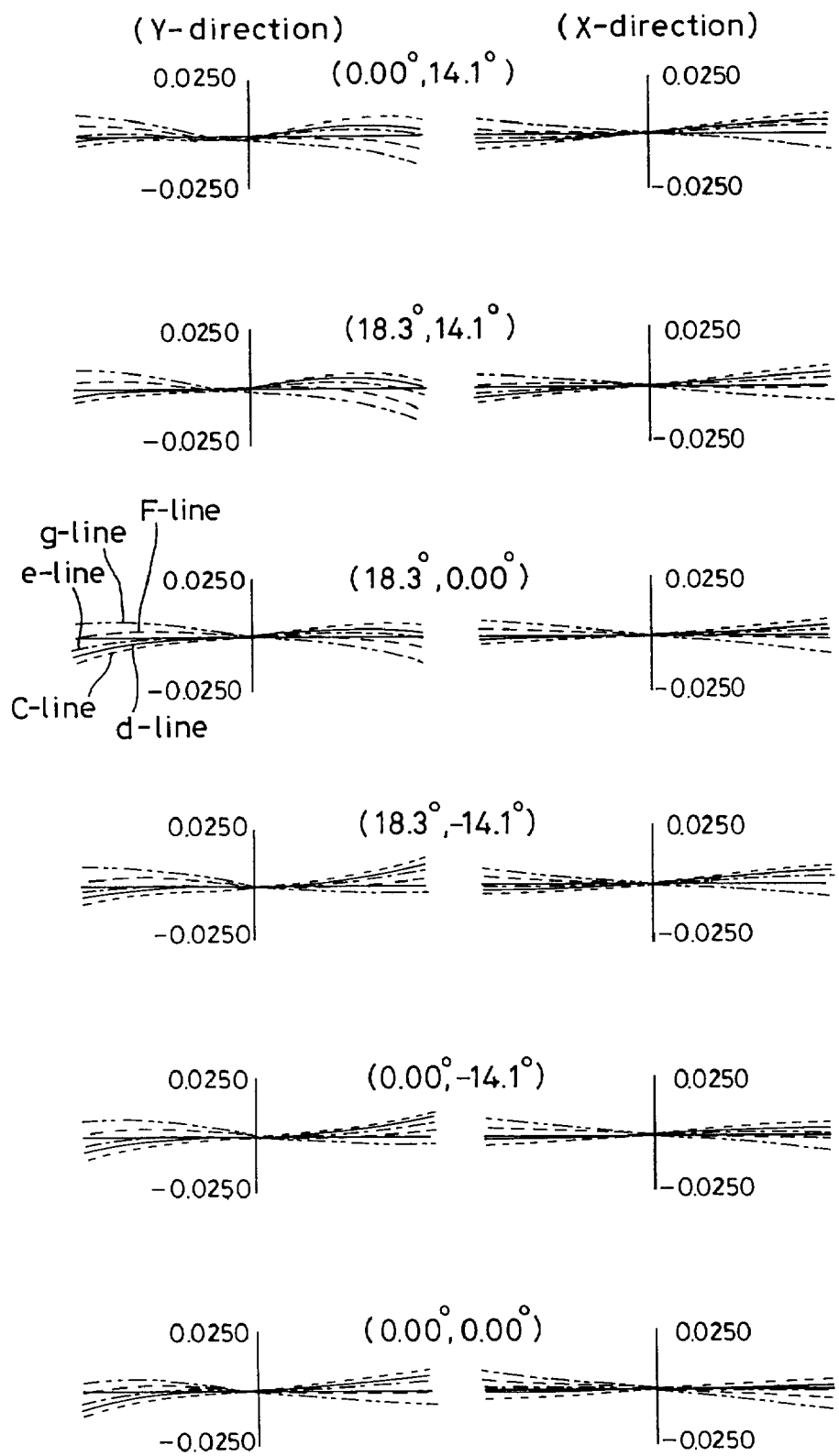
FIG. 3 is an aberrational diagram illustrating lateral aberrations in the image-forming optical system according to Example 1.
Figure 5A:
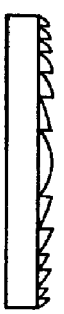
FIG. 5 is a diagram for describing the configurations of phase type optical low-pass filters.
Figure 5B:
Figure 5C:
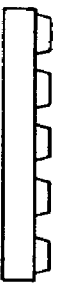
Figure 5D:
Figure 5E:
Figure 5F:
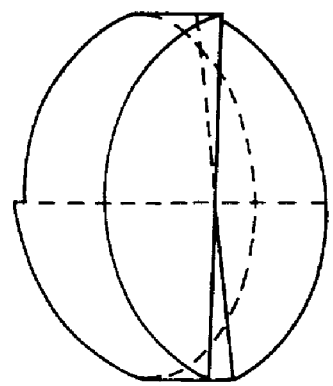
Figure 8:
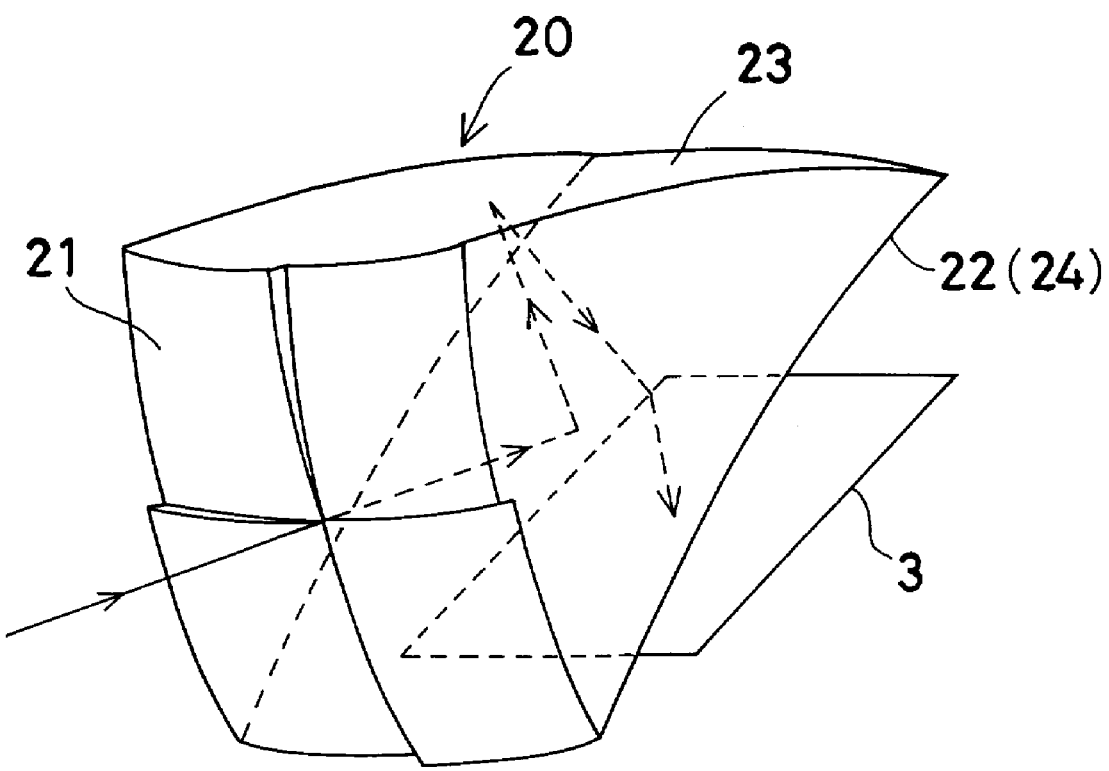
FIG. 8 is a schematic perspective view showing an arrangement in which a phase type optical low-pass filter is provided on an entrance surface of a prism.
Figure 9:
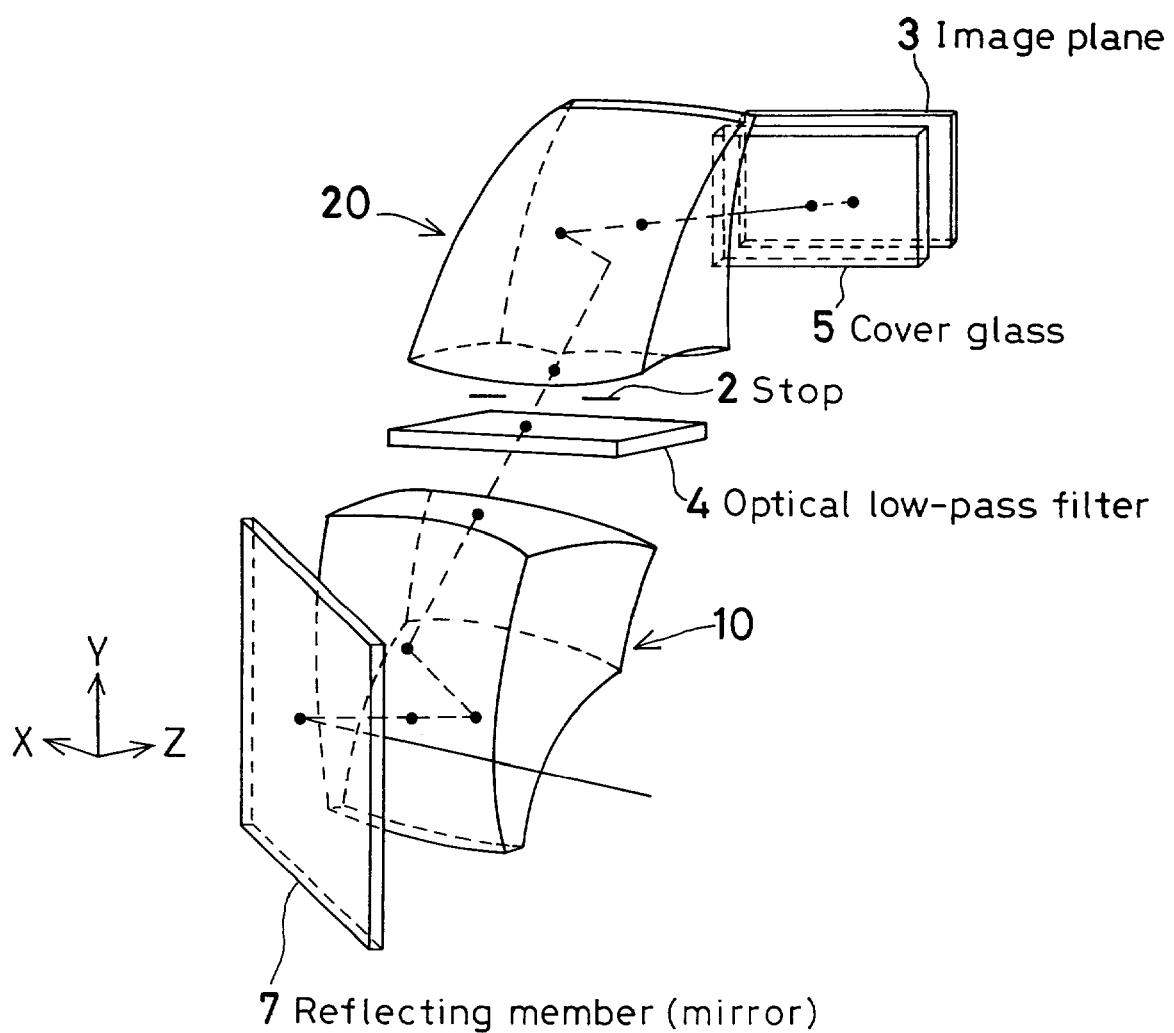
FIG. 9 is a sectional view showing a modification using a reflecting member for folding an optical path.
Figure 10:
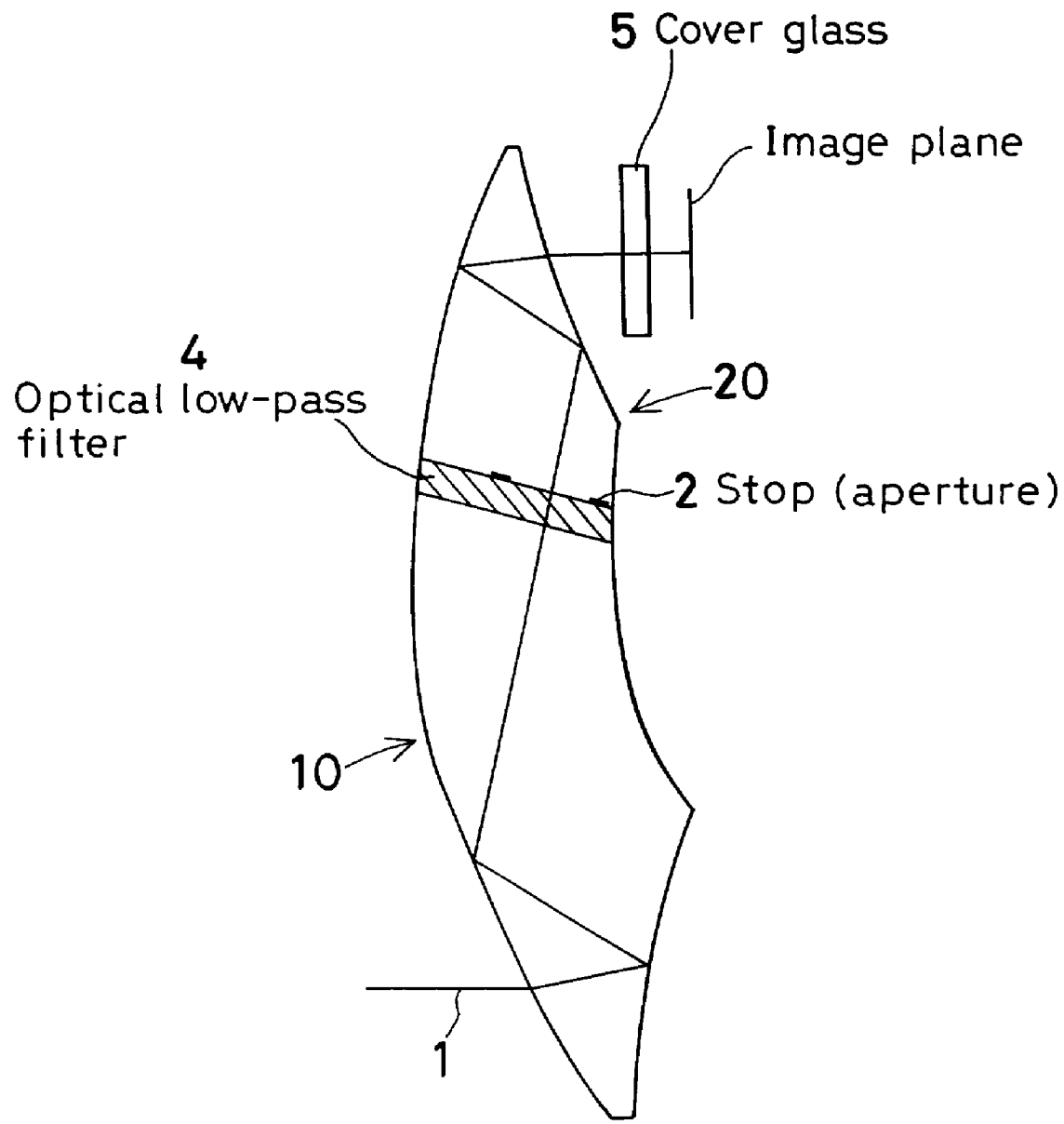
FIG. 10 is a sectional view showing a modification in which a stop, an optical low-pass filter and a plurality of prisms are integrated into one prism.

FIG. 3 is an aberrational diagram showing lateral aberrations in the above-described Example 1. In the aberrational diagram, the numerals in the parentheses denote [horizontal (X-direction) field angle, vertical (Y-direction) field angle], and lateral aberrations at the field angles are shown. The aberrational diagram shows, in order from the bottom toward the top of the diagram, lateral aberrations in the center of the image field; lateral aberrations at the position of minus about 70% of the image height on the Y-axis; lateral aberrations at the position of about 70% of the image height in the X-direction and minus about 70% of the image height in the Y-direction; lateral aberrations at the position of about 70% of the image height on the X-axis; lateral aberrations at the position of about 70% of the image height in the X-direction and about 70% of the image height in the Y-direction; and lateral aberrations at the position of about 70% of the image height on the Y-axis.

The surface Nos. 3, 4, 10 and 11 in the above-described Example 1 have the following values for $\theta$ in the condition (1-1) and $\Theta$ in the condition (2-1):

| Surface No. 3:  | $\Theta$ = 20.713° |
|---|---|
| Surface No. 4:  | $\theta$ = 55.849° |
| Surface No. 10: | $\theta$ = 55.311° |
| Surface No. 11: | $\Theta$ = 20.183° |

Next, let us show an example of a mounting mechanism for integrally mounting the two prisms 10 and 20 of the image-forming optical system according to the present invention and an example of a mounting mechanism for integrally mounting a CCD at the position of the image plane. Part (a) of FIG. 11 is a perspective view showing the two prisms 10 and 20 before they are united into an integral structure. Part (b) of FIG. 11 is a rear view showing the prisms 10 and 20 after they have been united into an integral structure. The prism 10 has mounting portions 32 integrally provided on both side surfaces thereof outside the optical path during the process of molding the prism 10. The prism 20 also has mounting portions 31 provided on both side surfaces thereof outside the optical path during the process of molding the prism 20. The mounting portions 31 extend from the side surfaces of the prism 20 toward the other prism 10. Projections 33, for example, are provided on the respective distal ends of the mounting portions 31. The other mounting portions 32 are provided with holes 34 for receiving the projections 33 of the mounting portions 31. By virtue of this arrangement, the two prisms 10 and 20 are mechanically united into an integral structure by fitting the projections 33 of the mounting portions 31, which are outside the optical path of the prism 20, into the respective holes 34 of the mounting portions 32, which are outside the optical path of the prism 10, and then joining together the mounting portions 31 and 32 by fitting, bonding, screwing, hot caulking, or other securing method. Thus, the image-forming optical system becomes free from such a problem that the optical axes of the two prism 10 and 20 may be displaced relative to each other, or the spacing between the two prisms 10 and 20 may vary undesirably. In addition, the assembly operation becomes easy.

FIG. 12 is a perspective view showing an example of an arrangement in which a CCD, which is placed in the image plane of the image-forming optical system, is mechanically united with the integral structure of the two prisms 10 and 20, which are united as shown in FIG. 11. In this example, a mounting member 35 is secured to mounting portions 31 that are provided on both side surfaces of the prism 20 by integral molding to unite the two prism 10 and 20 into an integral structure. The mounting member 35 is secured to the mounting portions 31 by fitting, bonding, screwing, hot caulking, or other securing method. Then, a board 36 for supporting a CCD 37 is secured to the mounting member 35 similarly by fitting, bonding, screwing, hot caulking, or other securing method. In this way, the CCD 37 is mechanically united with the integral structure of the two prisms 10 and 20 so as to lie in the image plane of the image-forming optical system according to the present invention. Thus, the image-forming optical system becomes free from relative displacement of the optical axes of the two prisms 10 and 20 and a variation in the spacing therebetween. In addition, the assembly operation is facilitated.

Figure 13:
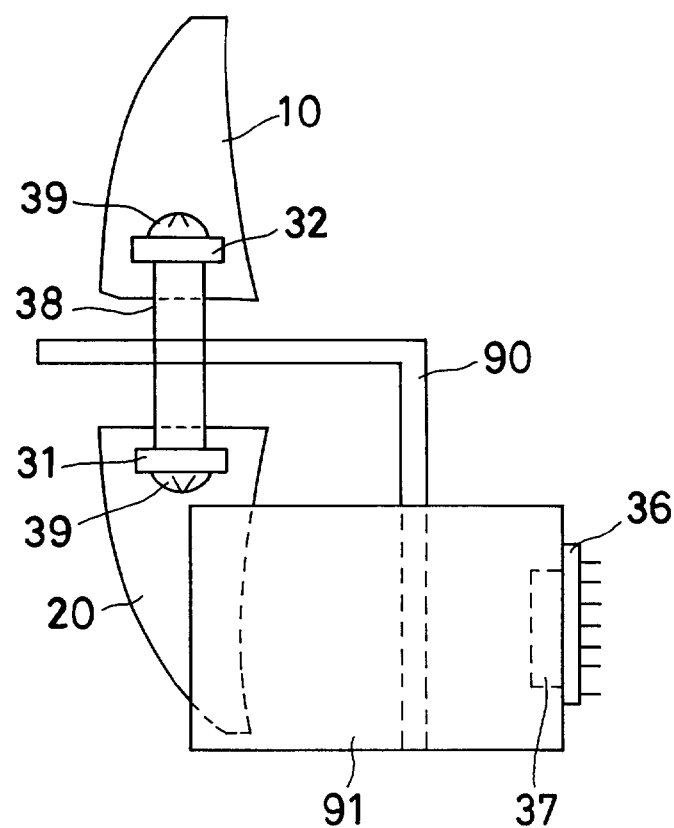
FIG. 13 is a side view showing another example of a mounting mechanism for mechanically uniting two prisms and a CCD into an integral structure.

FIG. 13 is a side view showing another example of a mounting mechanism wherein the two prisms 10 and 20 and the CCD 37 are mechanically united into an integral structure. Rod-shaped spacers 38 are placed between mounting portions 31 and 32 that are provided on side surfaces outside the optical paths of the two prisms 10 and 20 by integral molding, thereby setting a predetermined spacing between the mounting portions 31 and 32. Then, the mounting portions 31 and 32 and the rod-shaped spacers 38 are secured to each other by using screws 39, thereby mechanically uniting the two prisms 10 and 20 into an integral structure. A member 90 of L-shape as viewed from a side thereof is mechanically secured to the rod-shaped spacers 38. A mounting member 91 is secured to both sides of the member 90. The board 36 for supporting the CCD 37 is secured to the mounting member 91 by bonding, screwing, hot caulking, or other securing method. In this example, the mounting member 91 is arranged to sandwich the prism 20 at both side surfaces thereof, thereby enhancing the mounting stability.

Figure 14:
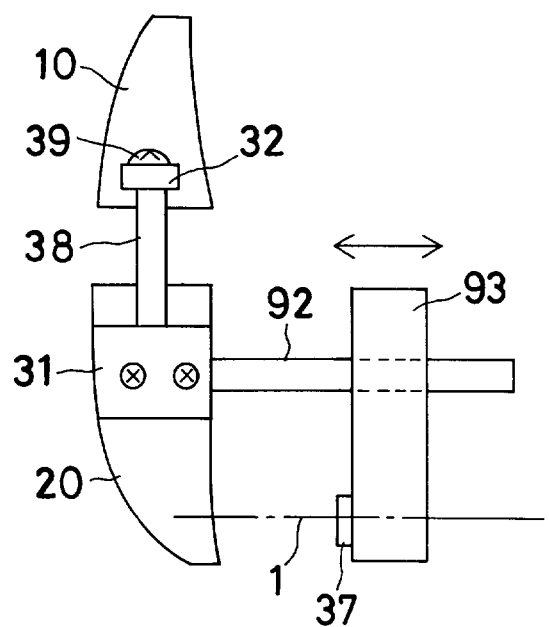
FIG. 14 is a diagram showing one example of a focusing mechanism usable in the image-forming optical system according to the present invention.

Next, an example of a focusing mechanism usable in the image-forming optical system according to the present invention will be described. FIG. 14 shows an example of an arrangement in which a CCD 37 is placed at the image side of an image-forming optical system having two prisms 10 and 20 united into an integral structure (the prisms 10 and 20 being united by a mechanism similar to that shown in FIG. 13), and focusing is effected by moving the CCD 37 in parallel to an optical axis 1 of light emanating from the prism 20. For example, shafts 92 are secured to mounting portions 31 provided on both side surfaces of the prism 20 such that the shafts 92 extend parallel to the optical axis 1. A movable block 93 is pierced with the shafts 92 so as to be movable along the shafts 92. The CCD 37 is secured to a surface of the movable block 93 that faces the prism 20. Focusing is performed by moving the movable block 93 back and forth along the shafts 92.

Figure 15:
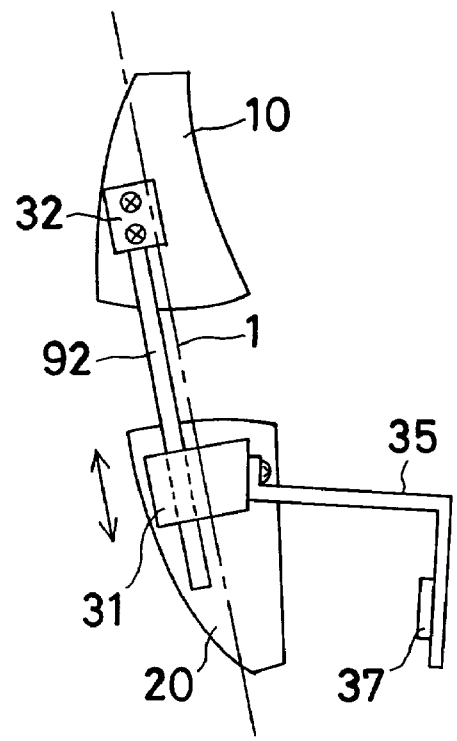
FIG. 15 is a diagram showing another example of a focusing mechanism usable in the image-forming optical system according to the present invention.

FIG. 15 shows an example of an arrangement in which focusing is effected by moving the second prism 20 relative to the first prism 10 in parallel to the axial principal ray 1 lying between the two prisms 10 and 20 of the image-forming optical system. In this example, the CCD 37 is integrally secured to the second prism 20 through a mechanism similar to that shown in FIG. 12. Shafts 92 are secured to mounting portions 32 provided on both side surfaces of the first prism 10 so as to extend parallel to the axial principal ray 1. Mounting portions 31 are provided on both side surfaces of the second prism 20 and pierced with the shafts 92 so that the second prism 20 is movable along the shafts 92. Focusing is performed by moving the second prism 20 back and forth along the shafts 92.

Figure 16:
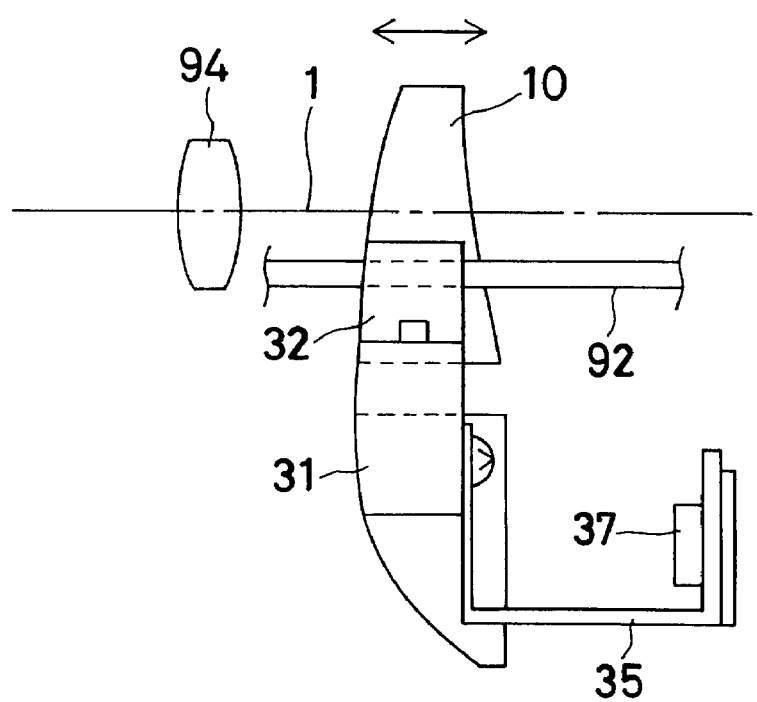
FIG. 16 is a diagram showing still another example of a focusing mechanism usable in the image-forming optical system according to the present invention.

FIG. 16 shows an example of an arrangement in which an optical system having two prisms 10 and 20 and a CCD 37 united into an integral structure by a mechanism such as those shown in FIGS. 11 to 13 is moved back and forth along the optical axis 1 of a lens 94 placed in front of the optical system. This is an example of focusing in a case where the image-forming optical system according to the present invention includes two prisms 10 and 20 and a lens 94 provided on the object side of the prisms 10 and 20. In this case, shafts 92 are secured to a photographic apparatus so as to extend parallel to the optical axis 1 of the lens 94. The shafts 92 extend through the mounting portions 32 so that the prisms 10 and 20 and the CCD 37 are movable as one unit along the shafts 92. Focusing is performed by moving the two prisms 10 and 20 and the CCD 37 back and forth along the shafts 92 as one unit.

The image-forming optical system according to the present invention can be arranged in the form of a zoom lens system. To form a zoom lens system, the first prism 10, the second prism 20, and the CCD 37 are arranged to be movable along the optical axis 1 so that the spacing between the first and second prisms 10 and 20 and the spacing between the second prism 20 and the CCD 37 vary in association with each other. For example, the mechanism shown in FIG. 14 and the mechanism shown in FIG. 15 are combined together and arranged to control the amount of movement of the second prism 20 relative to the first prism 10 and the amount of movement of the CCD 37 relative to the second prism 20 in association with each other.

Incidentally, the above-described image-forming optical system according to the present invention can be used in photographic apparatuses in which an object image formed by the image-forming optical system is received with a solid-state image pickup device, e.g. a CCD, to take a photograph of the object. In particular, the image-forming optical system can be used in cameras and endoscopes. Embodiments in which the present invention is applied to such apparatuses will be described below.

Figure 17:
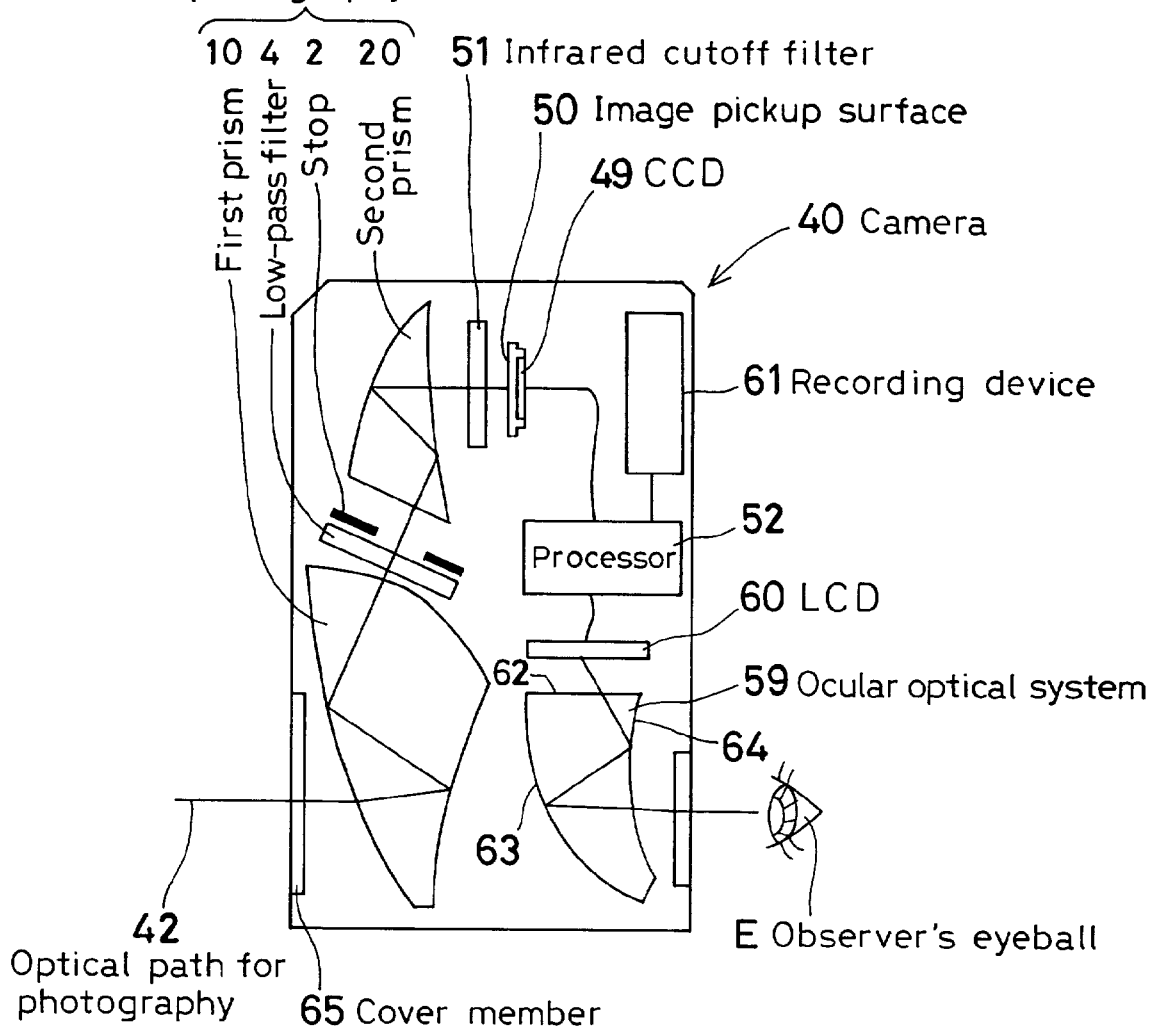
FIG. 17 is a conceptual view of an electronic camera to which the image-forming optical system according to the present invention is applied.

FIG. 17 is a conceptual view showing an arrangement in which an image-forming optical system according to the present invention is incorporated into an objective optical system 48 of a photography part of an electronic camera 40. In this example, the image-forming optical system shown in Example 1 is used as the objective optical system 48 for photography placed in an optical path 42 for photography. An object image produced by the objective optical system 48 for photography is formed on an image pickup surface 50 of a CCD 49 through a filter 51, e.g. an infrared cutoff filter. The object image received by the CCD 49 is processed in a processor 52 and displayed in the form of an electronic image on a liquid crystal display device (LCD) 60. The processor 52 also controls a recording device 61 for recording the object image detected by the CCD 49 in the form of electronic information. The image displayed on the LCD 60 is led to an observer's eyeball E through an ocular optical system 59. The ocular optical system 59 is formed from a decentered prism having a configuration similar to that used in the image-forming optical system according to the present invention. In this example, the ocular optical system 59 has three surfaces, i.e. an entrance surface 62, a reflecting surface 63, and a surface 64 serving as both reflecting and refracting surfaces. At least one of the two surfaces 63 and 64 having a reflecting action, preferably each of them, is formed from a plane-symmetry free-form surface with only one plane of symmetry that gives a power to a light beam and corrects aberrations due to decentration. The only one plane of symmetry is formed in approximately the same plane as the only one plane of symmetry of the plane-symmetry free-form surfaces in the prisms 10 and 20 of the objective optical system 48 for photography.

In the camera 40 arranged as stated above, the objective optical system 48 for photography can be constructed with a minimal number of optical members. Accordingly, a high-performance and low-cost camera can be realized. In addition, because all the constituent elements of the optical system can be arranged in the same plane, it is possible to reduce the thickness in a direction perpendicular to the plane in which the constituent elements are arranged.

Although in this example a plane-parallel plate is placed as a cover member 65 of the objective optical system 48 for photography, it is also possible to use a lens having a power as the cover member 65.

In the first prism 10 of the image-forming optical system according to the present invention, the surface closest to the object side may be used as a cover member instead of providing a cover member separately. In this case, however, the surface of the first prism 10 that is closest to the object side is the entrance surface of the first prism 10. Because the entrance surface is decentered with respect to the optical axis, if this surface is placed on the front side of the camera, it gives the illusion that the photographic center of the camera 40 is deviated from the subject when the entrance surface is seen from the subject side (the subject normally feels that photographing is being performed in a direction perpendicular to the entrance surface, as in the case of ordinary cameras). Thus, the entrance surface would give a sense of incongruity. Therefore, in a case where the surface of the image-forming optical system that is closest to the object side is a decentered surface as in this example, it is desirable to provide the cover member 65 from the viewpoint of preventing the subject from feeling incongruous when seeing the entrance surface, and allowing the subject to be photographed with the same feeling as in the case of the existing cameras.

Figure 18A:
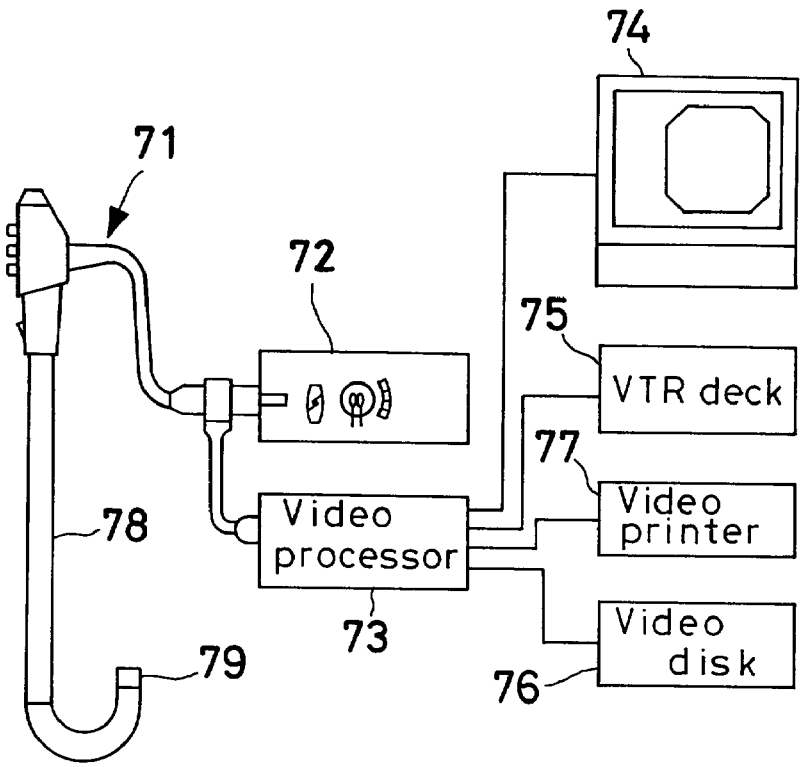
FIG. 18 is a conceptual view of a video endoscope system to which the image-forming optical system according to the present invention is applied.
Figure 18B:
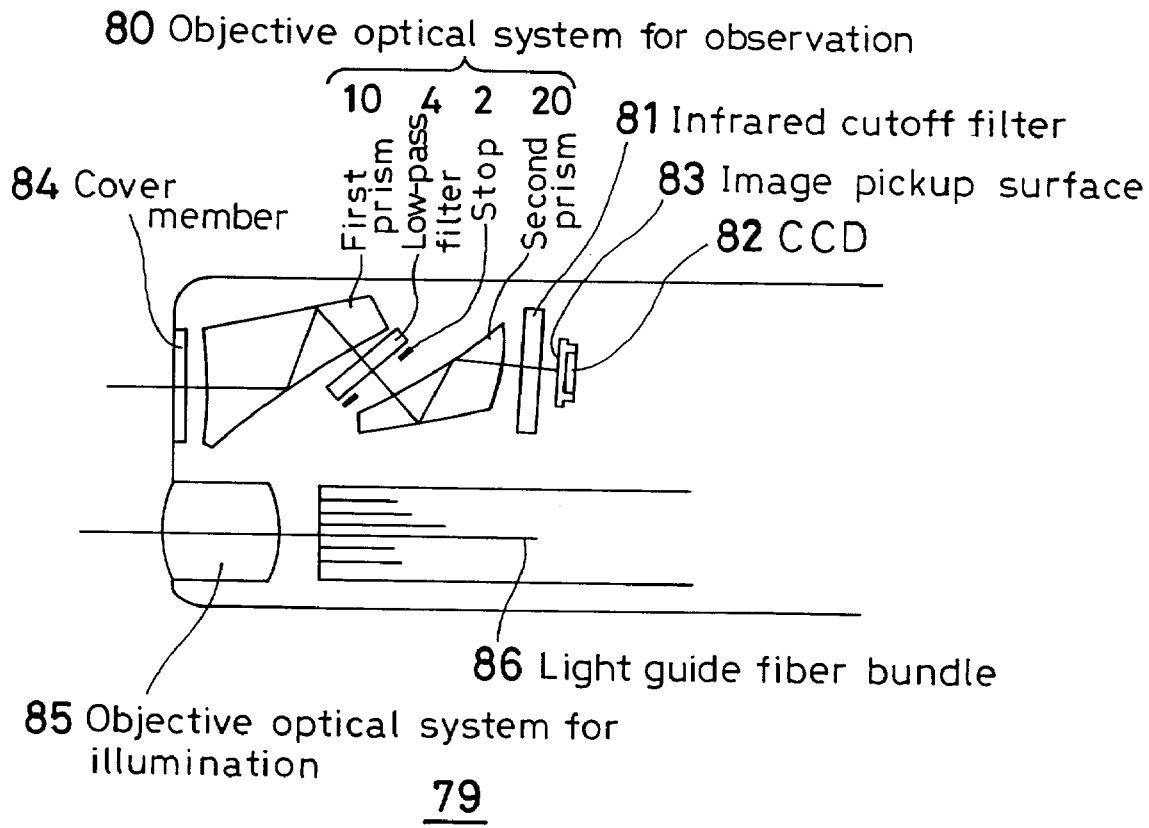

FIG. 18 is a conceptual view showing an arrangement in which the image-forming optical system according to the present invention is incorporated into an objective optical system 80 in an observation system of a video endoscope system. As shown in part (a) of FIG. 18, the video endoscope system includes a video endoscope 71, a light source unit 72 for supplying illuminating light, a video processor 73 for executing processing of signals associated with the video endoscope 71, a monitor 74 for displaying video signals outputted from the video processor 73, a VTR deck 75 and a video disk 76, which are connected to the video processor 73 to record video signals and so forth, and a video printer 77 for printing out video signals in the form of images. The video endoscope 71 has an insert part 78 with a distal end portion 79. The distal end portion 79 is arranged as shown in part (b) of FIG. 18. A light beam from the light source unit 72 passes through a light guide fiber bundle 86 and illuminates a part to be observed through an objective optical system 85 for illumination. Light from the part to be observed enters an objective optical system 80 for observation through a cover member 84. Thus, an object image is formed by the objective optical system 80. The object image is formed on an image pickup surface 83 of a CCD 82 through a filter 81, e.g. an infrared cutoff filter. Furthermore, the object image is converted into a video signal by the CCD 82. The video signal is displayed directly on the monitor 74 by the video processor 73, which is shown in part (a) of FIG. 18. In addition, the video signal is recorded in the VTR deck 75 and on the video disk 76 and also printed out in the form of an image from the video printer 77.

The endoscope arranged as stated above can be constructed with a minimal number of optical members. Accordingly, a high-performance and low-cost endoscope can be realized. Moreover, because the first prism 10 and the second prism 20, which constitute the image-forming optical system 80, are arranged in series in the direction of the longitudinal axis of the endoscope, the above-described advantageous effects can be obtained without hindering the achievement of a reduction in the diameter of the endoscope. Although in this example a plane-parallel plate is placed as the cover member 84, it is also possible to use a lens having a power as the cover member 84.

Figure 19:
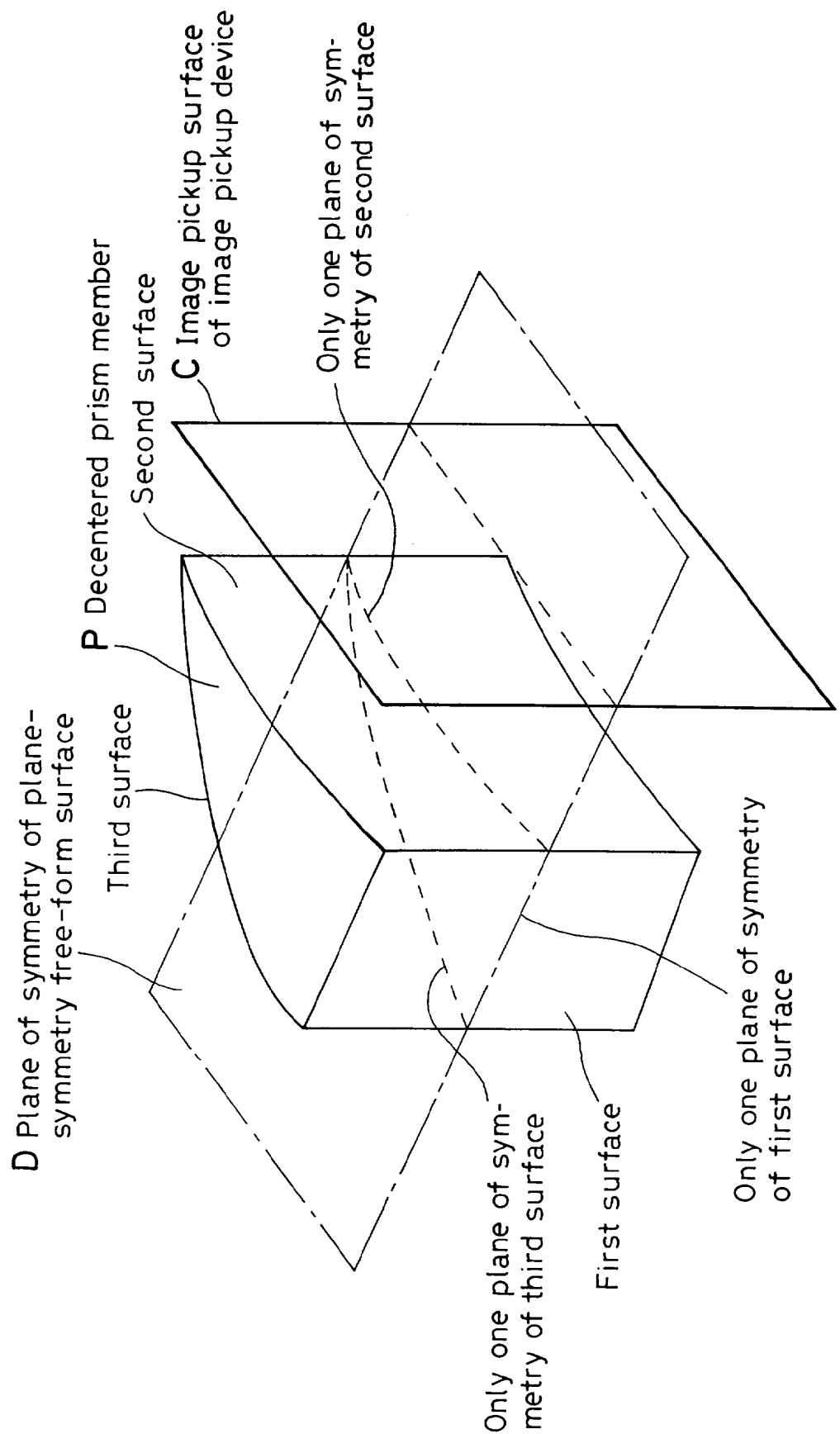
FIG. 19 is a diagram showing a desirable arrangement for the image-forming optical system according to the present invention when it is placed in front of an image pickup device.
Figure 20:
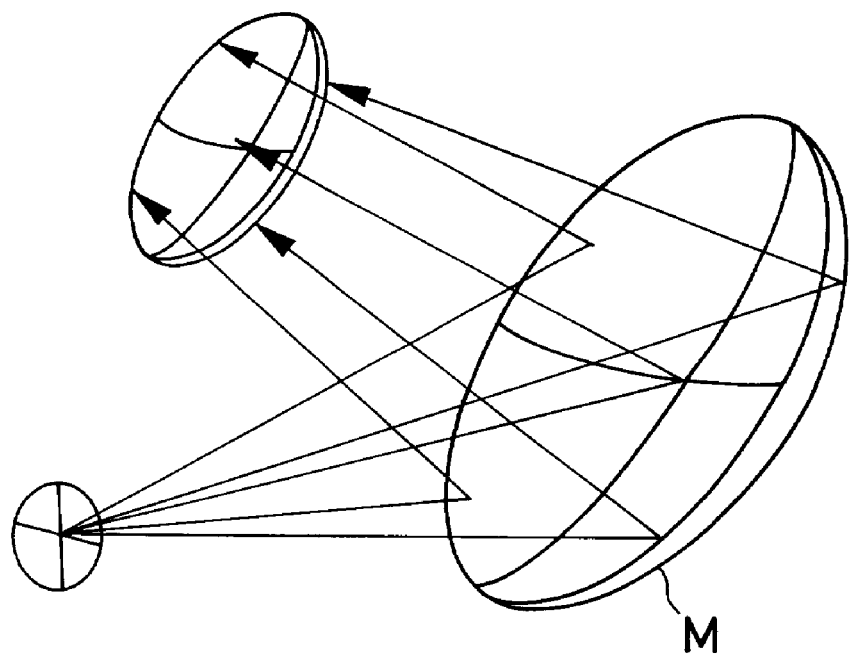
FIG. 20 is a conceptual view for describing curvature of field produced by a decentered reflecting surface.
Figure 21:
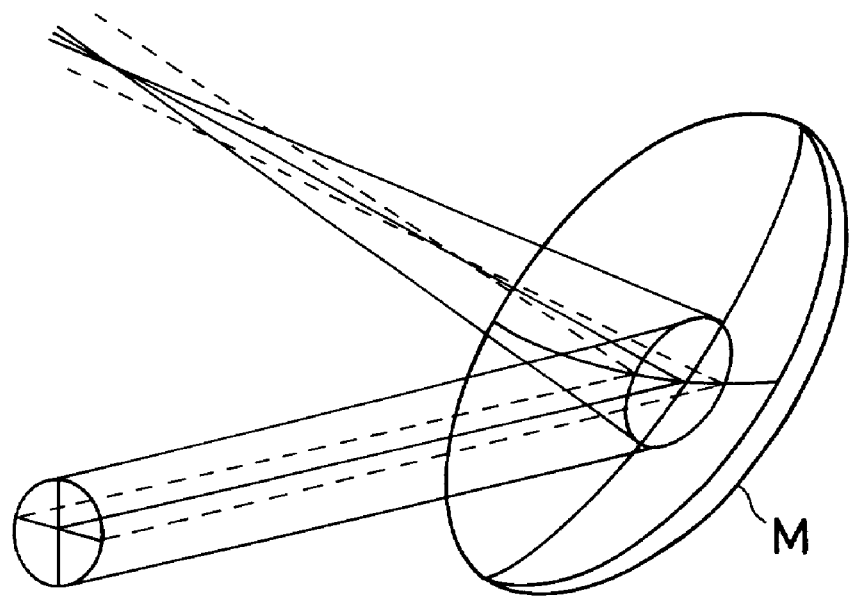
FIG. 21 is a conceptual view for describing astigmatism produced by a decentered reflecting surface.
Figure 22:
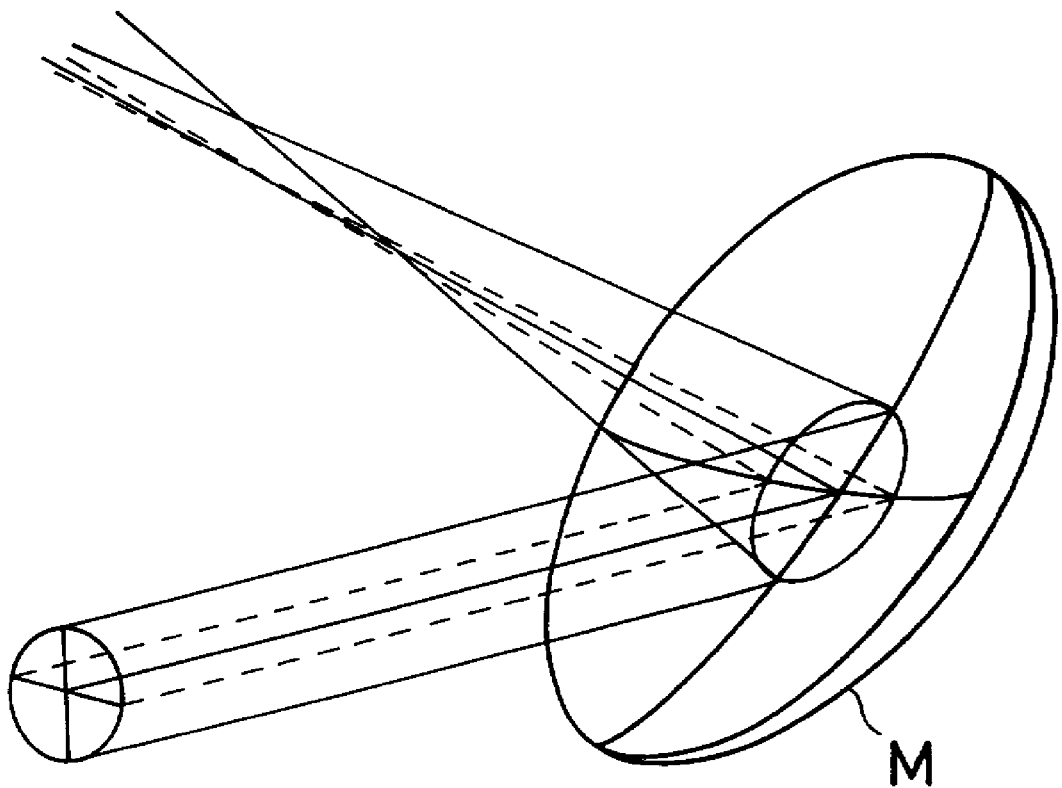
FIG. 22 is a conceptual view for describing coma produced by a decentered reflecting surface.

FIG. 19 is a diagram showing a desirable arrangement for the image-forming optical system according to Example 1 and so forth when the image-forming optical system is placed in front of an image pickup device, e.g. a CCD, or a filter. In the figure, a decentered prism P is a decentered prism placed on the object or image side of the stop in the image-forming optical system according to the present invention. When the image pickup surface C of an image pickup device forms a quadrangle as shown in the figure, it is desirable from the viewpoint of forming a beautiful image to place the decentered prism P so that the plane D of symmetry of a plane-symmetry free-form surface provided in the decentered prism P is parallel to at least one of the sides forming the quadrangular image pickup surface C.

When the image pickup surface C has a shape in which each of the four interior angles is approximately 90 degrees, such as a square or a rectangle, it is desirable that the plane D of symmetry of the plane-symmetry free-form surface should be parallel to two sides of the image pickup surface C that are parallel to each other. It is more desirable that the plane D of symmetry should lie at the middle between two parallel sides and coincide with a position where the image pickup surface C is in a symmetry between the right and left halves or between the upper and lower halves. The described arrangement enables the required assembly accuracy to be readily obtained when the image-forming optical system is incorporated into an apparatus, and is useful for mass-production.

When a plurality or all of the optical surfaces constituting the decentered prism P, i.e. the first surface, the second surface, the third surface, and so forth, are plane-symmetry free-form surfaces, it is desirable from the viewpoint of design and aberration correcting performance to arrange the decentered prism P so that the planes of symmetry of the plurality or all of the optical surfaces are in the same plane D. In addition, it is desirable that the plane D of symmetry and the image pickup surface C should be in the above-described relationship.

All the decentered prisms placed on the object and image sides of the stop in the image-forming optical systems in the above-described examples are of the type in which there are two internal reflections and which has three optical surfaces, one of which is formed from a surface having both a totally reflecting action and a transmitting action. It should, however, be noted that decentered prisms usable in the present invention are not necessarily limited to the described type.

As has been stated above, and as will be clear from the examples, the present invention makes it possible to obtain a compact, thin and low-cost image-forming optical system having an optical low-pass filter.

What we claim is:

1. An image-forming optical system for forming an image of an object, said image-forming optical system comprising:
   a stop;
   an object-side reflecting surface placed closer to an object side of said image-forming optical system than said stop, said object-side reflecting surface being a reflecting surface with an aspherical surface configuration that gives a power to a light beam when reflecting it;
   an image-side reflecting surface placed closer to an image side of said image-forming optical system than said stop, said image-side reflecting surface being a reflecting surface with an aspherical surface configuration that gives a power to a light beam when reflecting it; and
   a low-pass filter for cutting off a high-frequency component, said low-pass filter being provided between said object-side reflecting surface and said image-side reflecting surface.

2. An image-forming optical system for forming an image of an object, said image-forming optical system comprising:
   a stop;
   a first prism placed closer to an object side of said image-forming optical system than said stop, said first prism having an object-side reflecting surface with an aspherical surface configuration that reflects a light beam in said first prism and gives a power to the light beam when reflecting it;
   a second prism placed closer to an image side of said image-forming optical system than said stop, said second prism having an image-side reflecting surface with an aspherical surface configuration that reflects a light beam in said second prism and gives a power to the light beam when reflecting it; and
   a low-pass filter for cutting off a high-frequency component, said low-pass filter being provided between said object-side reflecting surface and said image-side reflecting surface.

3. An image-forming optical system according to claim 2, wherein said low-pass filter is placed between said first prism and said second prism.

4. An image-forming optical system according to claim 2, wherein said low-pass filter is formed on an entrance surface of said second prism.

5. An image-forming optical system according to claim 2, wherein said low-pass filter is formed on an exit surface of said first prism.

6. An image-forming optical system according to any one of claims 1 to 3, wherein said low-pass filter is placed on or near said stop.

7. An image-forming optical system according to claim 2, wherein at least one of the object-side reflecting surface of said first prism and the image-side reflecting surface of said second prism is formed from a surface having both transmitting and reflecting actions.

8. An image-forming optical system according to claim 2, wherein both the object-side reflecting surface of said first prism and the image-side reflecting surface of said second prism are formed from surfaces each having both transmitting and reflecting actions.

9. An image-forming optical system according to claim 7 or 8, wherein said surface having both transmitting and reflecting actions is a totally reflecting surface.

10. An image-forming optical system according to any one of claims 1 to 3, wherein said low-pass filter is a phase type optical low-pass filter.

11. An image-forming optical system according to any one of claims 1 to 3, wherein at least one of said reflecting surfaces with an aspherical surface configuration is decentered with respect to an optical axis and has a rotationally asymmetric curved surface configuration.

12. An image-forming optical system according to claim 11, wherein said reflecting surface having a rotationally asymmetric curved surface configuration is a plane-symmetry free-form surface having only one plane of symmetry, which is arranged to correct decentration aberrations produced by a decentered surface having a power.

13. An image-forming optical system according to any one of claims 1 to 3, wherein both said object-side reflecting surface and said image-side reflecting surface are formed from plane-symmetry free-form surfaces each having only one plane of symmetry, wherein the only one plane of symmetry of said plane-symmetry free-form surface that forms said object-side reflecting surface and the only one plane of symmetry of said plane-symmetry free-form surface that forms said image-side reflecting surface are in approximately an identical plane.

14. An image-forming optical system according to claim 2, wherein said first prism has at least two reflecting surfaces, both said at least two reflecting surfaces having a rotationally asymmetric curved surface configuration that gives a power to a light beam and has an aberration correcting action.

15. An image-forming optical system according to claim 2, wherein said second prism has at least two reflecting surfaces, both said at least two reflecting surfaces having a rotationally asymmetric curved surface configuration that gives a power to a light beam and has an aberration correcting action.

16. An image-forming optical system according to claim 14 or 15, wherein the rotationally asymmetric curved surface configuration of said at least two reflecting surfaces provided in said prism is formed from a plane-symmetry free-form surface having only one plane of symmetry, wherein the only one plane of symmetry of one of said at least two reflecting surfaces and the only one plane of symmetry of at least one other of said reflecting surfaces are in approximately an identical plane.

17. An image-forming optical system according to claim 12, which has an electronic image pickup device placed in an image plane, said electronic image pickup device having a quadrangular shape, wherein the only one plane of symmetry of each of said plane-symmetry free-form surfaces is approximately parallel to at least one side of said quadrangular shape.

18. An image-forming optical system according to any one of claims 1 to 3, which is a single focal length optical system.

19. A photographic apparatus having the image-forming optical system of any one of claims 1 to 5, wherein said image-forming optical system is placed in an image pickup part of an image pickup apparatus.

20. A camera apparatus having the photographic apparatus of claim 19, wherein said photographic apparatus has a camera mechanism.

* * * * *